United States Patent
Dempsey et al.

(10) Patent No.: US 9,271,817 B2
(45) Date of Patent: *Mar. 1, 2016

(54) TISSUE AUGMENTATION DEVICES AND METHODS

(75) Inventors: Ryan Dempsey, Westfield, IN (US); Jeffrey Miller, East Haven, CT (US); Steve Chen, Westfield, IN (US); Umesh H. Patel, West Lafayette, IN (US); F. Joseph Obermiller, West Lafayette, IN (US); Bhavin Shah, West Lafayette, IN (US); Chad E. Johnson, West Lafayette, IN (US)

(73) Assignee: Cook Biotech Incorporated, West Lafayette, IN (US)

( * ) Notice: Subject to any disclaimer, the term of this patent is extended or adjusted under 35 U.S.C. 154(b) by 1153 days.

This patent is subject to a terminal disclaimer.

(21) Appl. No.: 12/114,456

(22) Filed: May 2, 2008

(65) Prior Publication Data
US 2008/0248079 A1 Oct. 9, 2008

Related U.S. Application Data

(63) Continuation-in-part of application No. 11/481,422, filed on Jul. 5, 2006, now Pat. No. 7,850,985.

(60) Provisional application No. 60/696,606, filed on Jul. 5, 2005.

(51) Int. Cl.
*A61F 2/00* (2006.01)
*A61M 25/01* (2006.01)
(Continued)

(52) U.S. Cl.
CPC ......... *A61F 2/0059* (2013.01); *A61B 17/06004* (2013.01); *A61B 2017/06052* (2013.01);
(Continued)

(58) Field of Classification Search
CPC ........... A61F 2/0059; A61F 2/08; A61F 2/02; A61F 2002/4624; A61F 2002/30062; A61F 2210/0004; A61F 2/105; A61F 2/30756; A61L 27/3683; A61L 27/3604; A61L 27/3645; A61L 27/52; A61L 29/145; A61L 31/145; A61L 15/42; A61L 17/06; A61L 27/3662; A61L 27/3666; A61L 27/3687; A61L 27/3691; A61L 27/3695; A61L 27/60; A61L 27/24; A61L 27/3633; A61L 27/3641; A61M 5/32; A61M 2025/018; A61M 25/0662; A61B 17/06066; A61B 17/3468; A61B 2017/00004; A61B 2017/00792; A61B 17/06004; A61B 2017/06052; A61B 17/8822; A61B 17/0057; A61K 19/1635; A61K 9/1652; C08B 37/00; C08B 37/0084; C08J 2300/14; C08J 3/03; C08J 3/243; C08H 1/06; D02G 1/00; Y10S 530/84; Y10S 530/842; Y10S 623/915

See application file for complete search history.

(56) References Cited

U.S. PATENT DOCUMENTS 3,875,946 A 4/1975 Duncan
3,980,177 A 9/1976 McGregor
(Continued)

FOREIGN PATENT DOCUMENTS

EP 0064860 A2 * 11/1982

OTHER PUBLICATIONS

W.L. Gore & Associates, Inc., GORE Subcutaneous Augmentation Material catalog, Jun. 2002, pp. 1-6.
(Continued)

*Primary Examiner* — Louise W Humphrey
*Assistant Examiner* — Aaron J Kosar
(74) *Attorney, Agent, or Firm* — Woodard Emhardt Moriarty McNett & Henry LLP

(57) ABSTRACT

Tissue augmentation devices, as well as methods of manufacturing and using the same, are disclosed. In certain embodiments, a tissue augmentation device comprises an elongate tissue penetrating member and an amount of remodelable material, wherein at least a portion of the elongate member is cannulated, and at least a portion of the amount of material is received within at least a portion of the cannulated portion of the elongate member. The elongate tissue penetrating member may provide at least one deformation that is configured to constrict portions of the amount of remodelable material received within the elongate member. In alternate embodiments, a flexible covering over an implantable biomaterial provides protection and allows an easier delivery of the biomaterial to a tissue tract.

20 Claims, 12 Drawing Sheets

(51) Int. Cl.
  *A61L 27/24* (2006.01)
  *A61F 2/02* (2006.01)
  *A61B 17/06* (2006.01)
  *A61M 25/06* (2006.01)
  *A61M 5/32* (2006.01)

(52) U.S. Cl.
  CPC .. *A61F2/02* (2013.01); *A61L 27/24* (2013.01); *A61M 5/32* (2013.01); *A61M 25/0662* (2013.01); *A61M 2025/018* (2013.01); *Y10S 623/915* (2013.01)

(56) References Cited

U.S. PATENT DOCUMENTS

| | | | |
|---|---|---|---|
| 4,405,314 A | 9/1983 | Cope | |
| 4,792,336 A | 12/1988 | Hlavacek et al. | |
| 4,902,508 A | 2/1990 | Badylak et al. | |
| 4,956,178 A | 9/1990 | Badylak et al. | |
| 4,980,403 A * | 12/1990 | Bateman et al. | 524/17 |
| 5,281,422 A | 1/1994 | Badylak et al. | |
| 5,536,582 A | 7/1996 | Prasad et al. | |
| 5,554,389 A | 9/1996 | Badylak et al. | |
| 5,607,477 A * | 3/1997 | Schindler et al. | 623/23.72 |
| 5,711,969 A | 1/1998 | Patel et al. | |
| 5,755,791 A | 5/1998 | Whitson et al. | |
| 5,855,619 A | 1/1999 | Caplan et al. | |
| 5,955,110 A | 9/1999 | Patel et al. | |
| 5,968,096 A | 10/1999 | Whitson et al. | |
| 6,090,996 A * | 7/2000 | Li | A61L 31/044 606/151 |
| 6,099,567 A | 8/2000 | Badylak et al. | |
| 6,206,931 B1 | 3/2001 | Cook et al. | |
| 6,231,613 B1 | 5/2001 | Greff et al. | |
| 6,241,734 B1 * | 6/2001 | Scribner et al. | 606/93 |
| 6,368,356 B1 * | 4/2002 | Zhong et al. | 623/23.75 |
| 6,375,989 B1 | 4/2002 | Badylak et al. | |
| 6,475,232 B1 | 11/2002 | Babbs et al. | |
| 7,850,985 B2 * | 12/2010 | Patel et al. | 424/423 |
| 8,470,356 B2 * | 6/2013 | Patel et al. | 424/423 |
| 2002/0019670 A1 | 2/2002 | Crawley et al. | |
| 2002/0103542 A1 * | 8/2002 | Bilbo | 623/23.72 |
| 2004/0006353 A1 | 1/2004 | Bosley et al. | |
| 2004/0176856 A1 * | 9/2004 | Raphael et al. | 623/23.72 |
| 2005/0021141 A1 | 1/2005 | Bleyer et al. | |
| 2005/0049638 A1 | 3/2005 | Mandelbaum | |
| 2005/0159776 A1 | 7/2005 | Armstrong | |
| 2006/0058890 A1 | 3/2006 | Lesh | |
| 2008/0248079 A1 | 10/2008 | Dempsey et al. | |
| 2011/0125289 A1 * | 5/2011 | Armstrong | A61B 17/0057 623/23.72 |

OTHER PUBLICATIONS

Lotters et al., "The mechanical properties of the rubber elastic polymer polydimethylsiloxane for sensor applications," J. Micromech. Microeng. 7 (1997) 145-147, printed in UK.

* cited by examiner

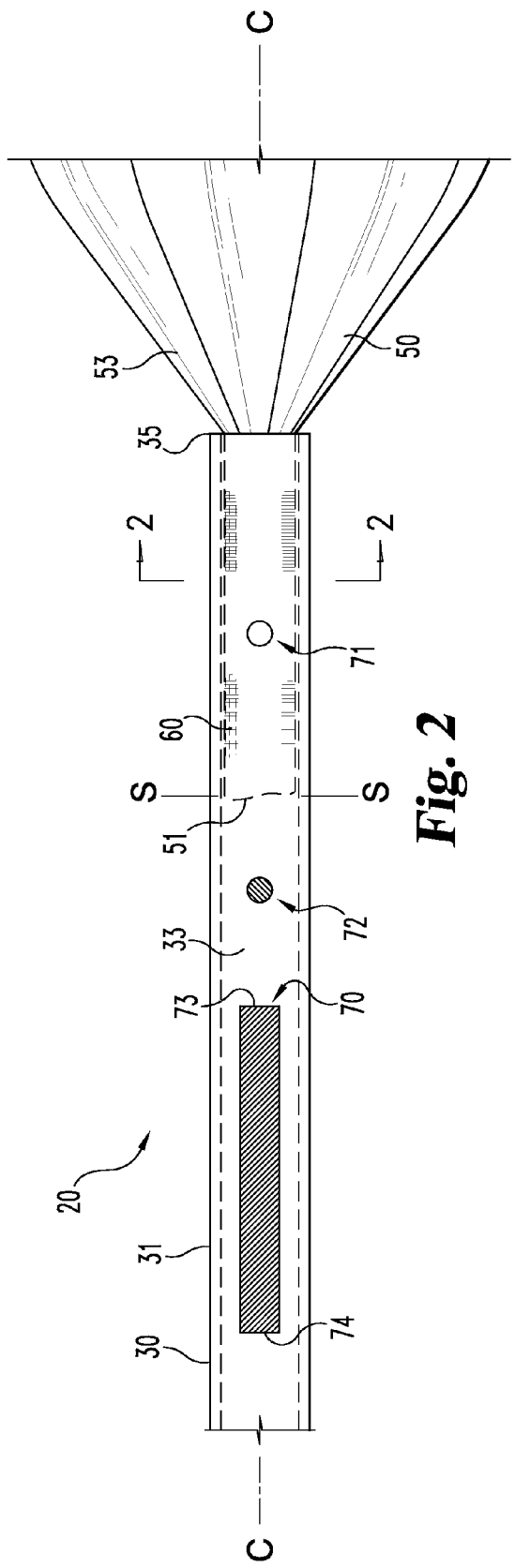
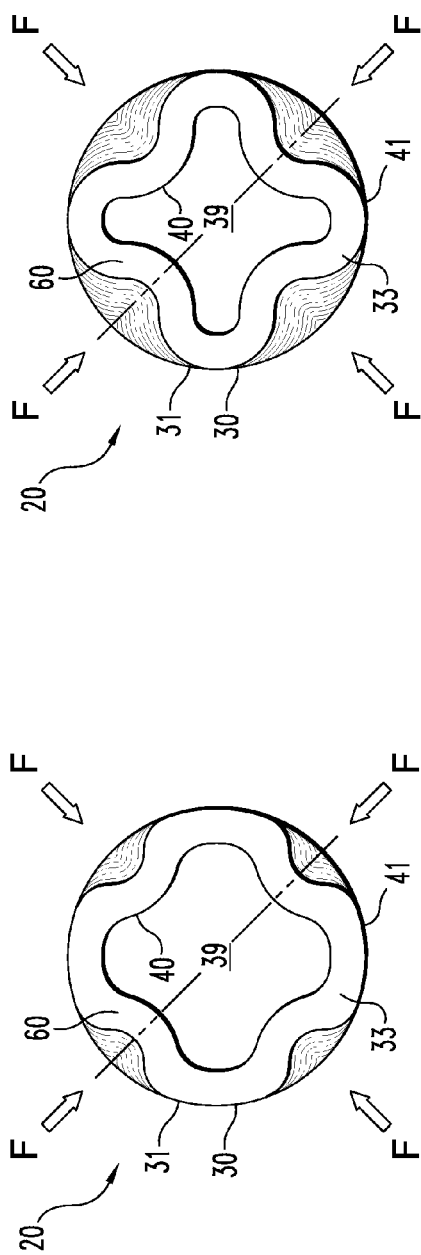
Fig. 2
Fig. 3a
Fig. 3b

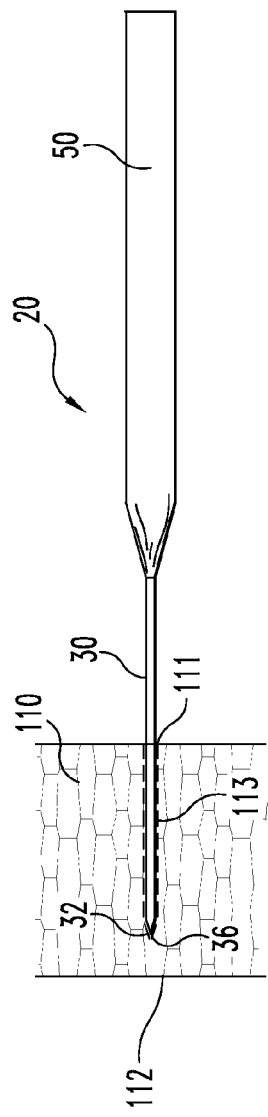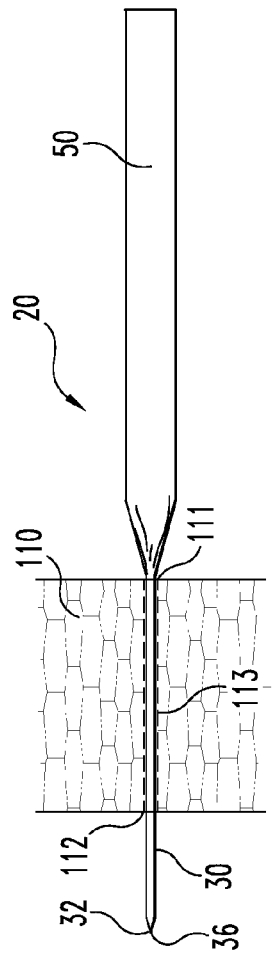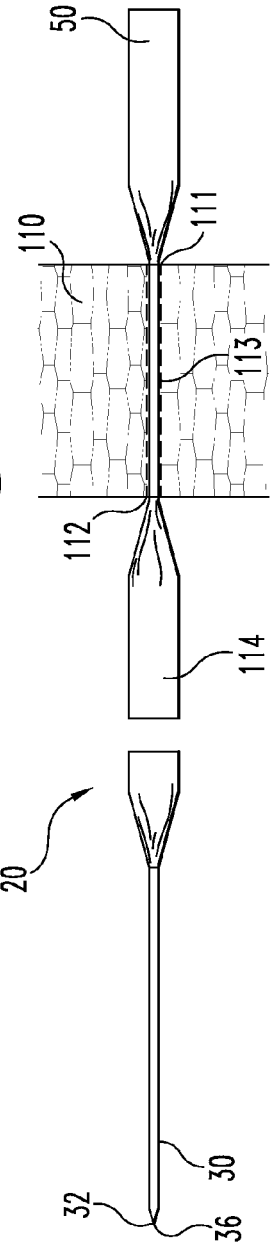

TISSUE AUGMENTATION DEVICES AND METHODS

REFERENCE TO RELATED APPLICATION

The present application is a continuation-in-part patent application of U.S. patent application Ser. No. 11/481,422, filed Jul. 5, 2006, which claims benefit of U.S. Provisional Patent Application Ser. No. 60/696,606, filed Jul. 5, 2005.

BACKGROUND

The present invention resides generally in the field of medical devices, and in certain aspects relates more particularly to tissue augmentation devices, as well as methods of manufacturing and using the same.

Plastic surgery, including soft tissue augmentation, is a viable option for people who want to change their physical appearance. An increasingly popular form of plastic surgery is lip augmentation, a procedure to increase the fullness of the lips. Lips are augmented using a variety of techniques and materials. While some procedures offer a temporary fix, others provide a more permanent solution. Temporary lip augmentation often involves injecting a filler material into a lip, such as fat, collagen, hyaluronic acid, and particulated dermis or fascia.

Permanent lip augmentation eliminates or reduces some of the problems associated with temporary lip augmentation. One permanent lip augmentation technique involves injecting liquid silicone into the lip. However, liquid silicone is inherently difficult to remove from the lips should a problem arise or the patient desire removal. Further, liquid silicone injections carry a relatively high incidence of inflammation, migration, and even skin ulceration, which can occur many years later. Currently, liquid silicone is not FDA-approved for soft tissue augmentation, although it is still used outside the United States.

Other permanent lip augmentation techniques involve implanting various forms of expanded polytetraflouroethylene (PTFE) into the lip, such as Gore-Tex™ strips or Softform™ and Ultrasoft™ tubes. PTFE is porous to allow tissue ingrowth into the material, which in turn, prevents migration.

Apart from procedures involving fillers or implants, other surgical procedures, such as lip rolls, lip lifts, and micro pigmentation, and nonsurgical techniques, such as using lip pumps, have been used to try to enhance the lips.

In addition to augmenting lips, a variety of other procedures for altering the appearance of patient physical features are commonly undertaken, particularly in the facial area. These include, as illustrative examples, procedures to diminish or otherwise improve the appearance of wrinkles and/or nasal labial folds on the face.

In view of this background, there remain needs for improved and/or alternative tissue augmentation devices. The present invention is addressed to these needs.

SUMMARY

Accordingly, certain aspects of the present invention relate to devices and methods for augmenting patient tissue that include or involve the use of a segment of remodelable implant material coupled to a tissue penetrating member for positioning the remodelable implant material in patient tissue in an augmenting configuration. Thus, certain embodiments of the present invention relate to tissue augmentation devices that include a tissue penetrating member and an amount of remodelable material coupled thereto. The tissue penetrating member has a tip configured to penetrate tissue, and a cannula extending along at least part of its length. At least a portion of the remodelable material is received and secured within the cannula.

In advantageous embodiments, an inventive device is configured to provide tissue augmentation through active promotion of patient tissue formation. Such a device in accordance with certain inventive aspects comprises an elongate segment of angiogenic, remodelable collagenous biomaterial effective to promote patient tissue ingrowth into a region in which the biomaterial is implanted. The device also incorporates a needle including an elongate cannulated body having cannula walls and a distal open needle end, the needle further including a tapered proximal portion forming a tissue-penetrating needle tip. The segment of angiogenic, remodelable collagenous biomaterial has an internalized portion extending through the distal open needle end and received within the cannulated body, and a trailing portion occurring distal of the distal open needle end. The cannula walls of the cannulated body have at least one inwardly deformed or otherwise extending region constricting and securing the internalized portion of the angiogenic, remodelable collagenous biomaterial. In certain aspects, the segment of remodelable material can comprise a remodelable extracellular matrix (ECM) material, such as but not limited to small intestinal submucosa (SIS). The needle may also have one or more holes in its side wall through which a sterilizing agent may be passed.

In another embodiment, a method of augmenting tissue in a patient is provided. The method involves implanting a segment of remodelable material at a location where tissue augmentation is desired, using a tissue augmentation device having the segment coupled to an elongate tissue penetrating member such as a needle. In particular aspects, the segment is of a nature and is implanted at a location (e.g. a subcutaneous location) wherein a significant, visibly-discernable alteration of a surface feature of the patient's tissue is achieved, such alteration for example including an outward projection of patient tissue. In certain embodiments, an elongate segment of remodelable material is implanted underneath and in a plane generally parallel to an elongate surface feature of the patient, so as to result in an outward projection of the surface feature, e.g. as occurs in a human upper and/or lower lip augmentation procedure. In particular aspects, such methods of the invention can utilize tissue augmentation devices as described herein. Accordingly, a needle coupled to the remodelable segment of material can be passed through a volume of patient tissue, and thereby used to draw the segment of remodelable material, or at least a portion thereof, into the volume of tissue along a passageway formed by the needle. For example, the first end of the needle can be inserted into the volume of tissue through an entry point in the patient's skin. Thereafter, the first end of the needle can be forced out of the volume of tissue through an exit point in the patient's skin. The needle can then be withdrawn from the volume of tissue through the exit point, leaving at least a portion of the segment of material within the tissue passageway formed by the needle. At least a portion of the segment of material can then be separated from the tissue augmentation device.

In additional embodiments, inventive medical products for augmenting tissue are provided. The products include at least one tissue augmentation device as described herein, in a sealed package. The package may be configured to maintain the tissue augmentation device in a sterile condition.

In still other embodiments, the present invention provides methods for manufacturing a tissue augmentation device. An assembly is provided including a needle having an elongate cannulated body having cannula walls and a distal open needle end, the needle further including a tapered proximal portion forming a tissue-penetrating needle tip. The assembly also includes an elongate segment of angiogenic, remodelable collagenous biomaterial effective to promote patient tissue ingrowth into a region in which the biomaterial is implanted, wherein the segment of angiogenic, remodelable collagenous biomaterial has an internalized portion extending through the distal open needle end and received within the cannulated body, and a trailing portion occurring distal of the distal open needle end. The internalized portion is secured to the needle. In certain aspects, this securement is achieved by causing the cannula walls to change from a first configuration to a second configuration, wherein the second configuration compresses the collagenous biomaterial between cannula walls portions, e.g. wherein regions of the cannula walls extend inwardly to provide the second configuration which compresses the biomaterial. The inwardly extending wall regions can be provided by deformed wall portions, for example created by crimping, which can constrict and secure the internalized portion of the angiogenic, remodelable collagenous biomaterial.

In another embodiment, the invention provides a device useful for introducing an implantable material into soft tissue of a patient, such as for providing tissue augmentation. The device includes an elongate segment of an implantable biomaterial attached to a tissue-penetrating member such as a needle. The device also includes a flexible covering material received over at least a portion of the implantable biomaterial.

In another aspect, the invention provides a method for implanting a biocompatible implant material into soft tissue of a patient. The method includes creating an opening in skin of the patient and positioning a flexible covering material at least partially within the opening. The method further includes introducing a biocompatible implant material through the opening and into soft tissue of the patient, wherein said flexible covering material protects the biocompatible implant material from contact with skin tissue of the patient adjacent the opening.

In still other embodiments, the present invention provides devices for introducing implant material into soft tissue of a patient. One of these devices includes an implantable material and a tissue-penetrating member. The implantable material is comprised of a rolled sheet material, and the tissue-penetrating member is attached to the implantable material.

In one aspect, another inventive device for introducing implant material into soft tissue of a patient includes a leading portion and a trailing portion. The leading portion is configured to traverse a volume of patient tissue, and includes a tissue-penetrating member. The trailing portion extends from the leading portion, and includes a rolled sheet material. The leading portion is effective to draw at least a portion of the trailing portion into the volume of patient tissue along a passageway formed by the tissue-penetrating member. In some forms, an intermediate portion (e.g., a suture) connects the leading portion to the trailing portion.

In still another embodiment, an inventive device for introducing implant material into soft tissue of a patient includes a tissue-penetrating member and an implantable material that is secured to the tissue-penetrating member. The implantable material includes a first region in which the material is structurally weakened to facilitate separation of a first piece of material from the implantable material. In one aspect, the implantable material comprises a sheet material, and the first structurally weakened region comprises a first line of perforations occurring along part of the sheet material. In some forms, such a sheet material has a width dimension, and the first line of perforations is located on the sheet material such that separation of the first piece of material from the implantable material along the first line of perforations reduces this width dimension.

Additional embodiments as well as advantages of the present invention will be apparent from the detailed description and drawings included herein.

BRIEF DESCRIPTION OF THE DRAWINGS

FIG. 2 is a partial, front view of the tissue augmentation device of FIG. 1.

FIGS. 3(*a*)-(*b*) are top, sectional views of the tissue augmentation device of FIG. 1 along the view line 2-2 shown in FIG. 1.

FIGS. 6(*a*)-(*c*) are diagrams that illustrate steps in one tissue augmentation procedure of the invention.

DETAILED DESCRIPTION

Figure 1:
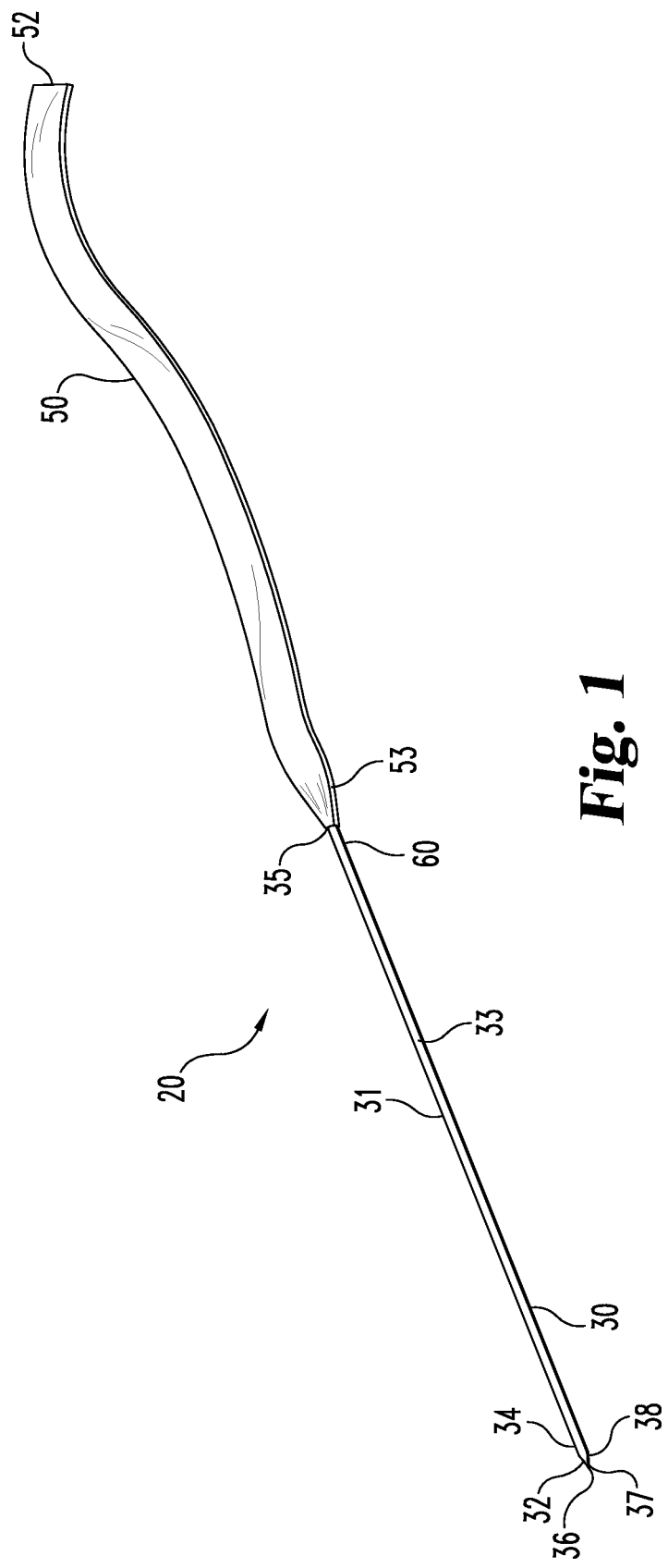
FIG. 1 is a perspective view of a tissue augmentation device.

While the present invention may be embodied in many different forms, for the purpose of promoting an understanding of the principles of the present invention, reference will now be made to the embodiments illustrated in the drawings, and specific language will be used to describe the same. It will nevertheless be understood that no limitation of the scope of the invention is thereby intended. Any alterations and further modifications in the described embodiments and any further applications of the principles of the present invention as described herein are contemplated as would normally occur to one skilled in the art to which the invention relates.

As disclosed above, the present invention provides tissue augmentation devices, as well as methods of manufacturing and using the same.

With reference now to FIG. 1, shown is a perspective view of one illustrative tissue augmentation device 20 of the present invention, which includes a needle 30 and a segment of biocompatible implant material 50. The needle 30 has a cannulated, elongate portion 31 and a tapered portion 32. The elongate portion 31 has a wall 33, a proximal end 34, and distal end 35. The tapered portion 32 has a first end 36, which forms a needle tip 37 and a second end 38 which is integral with the proximal end 34 of the elongate portion 31. It will be understood that the body of the needle 30 can be formed of a single, integral body or can be formed from multiple connected pieces. The needle tip 37 is desirably of the non-coring type, and in certain embodiments can include a closed tip, such as a trocar tip, having multiple facets, e.g. two, three or four facets, a smooth pencil tip, a blunt tip, a bullet tip (e.g. non-cutting) or any other suitable tip for forming a tract through soft tissue and/or for traversing an existing tract such as one formed by another needle or surgical tool. These or other needle tips can be formed upon or added to the end of a cannulated or solid needle body portion in accordance with the invention using conventional techniques such as welding, swaging, grinding, and/or any other suitable method.

The segment of material 50 has a leading end 51 (hidden in FIG. 1) and a trailing end 52. A portion of the segment of material 50, including the segment's leading end 51, is received within the distal end 35 of the elongate portion 31. The wall 33 of the elongate portion 31 provides a plurality of deformed regions 60 that are configured to compress and secure portions of the segment of material 50 received within the needle 30. Alternatively, a suitable material segment such as segment 50 may be secured to the outer surface of needle 30 or another suitable tissue penetrating device, e.g., one having a cannulated and/or non-cannulated body.

In certain embodiments, tissue augmentation devices of the invention include a flexible covering (e.g., a sheath made of a flexible material) received over a segment of biocompatible implant material. Such a flexible covering can be useful in reducing or eliminating contact of the segment of material with non-sterile objects at the treatment site during an implantation procedure. Such a reduction in contact may reduce the likelihood of bacterial contamination which could otherwise occur due to contact of the segment of material with outer surfaces of the patient's skin or other non-sterile surfaces. The flexible covering may also provide a more lubricious surface to aid in delivery of the segment of material through a tissue tract. In addition to providing the above benefits, a flexible covering can also be used in conjunction with means for indirectly attaching a segment of material to a needle or other tissue penetrating device by an attachment means, such as a suture, which has a predictable breaking strength. The use of an attachment means can provide the practitioner with more control over when and where the segment of material is disconnected from other portions of the tissue augmentation device (e.g., it can prevent premature disconnection between the needle and the segment of material to remain at the implant site).

Figure 8:
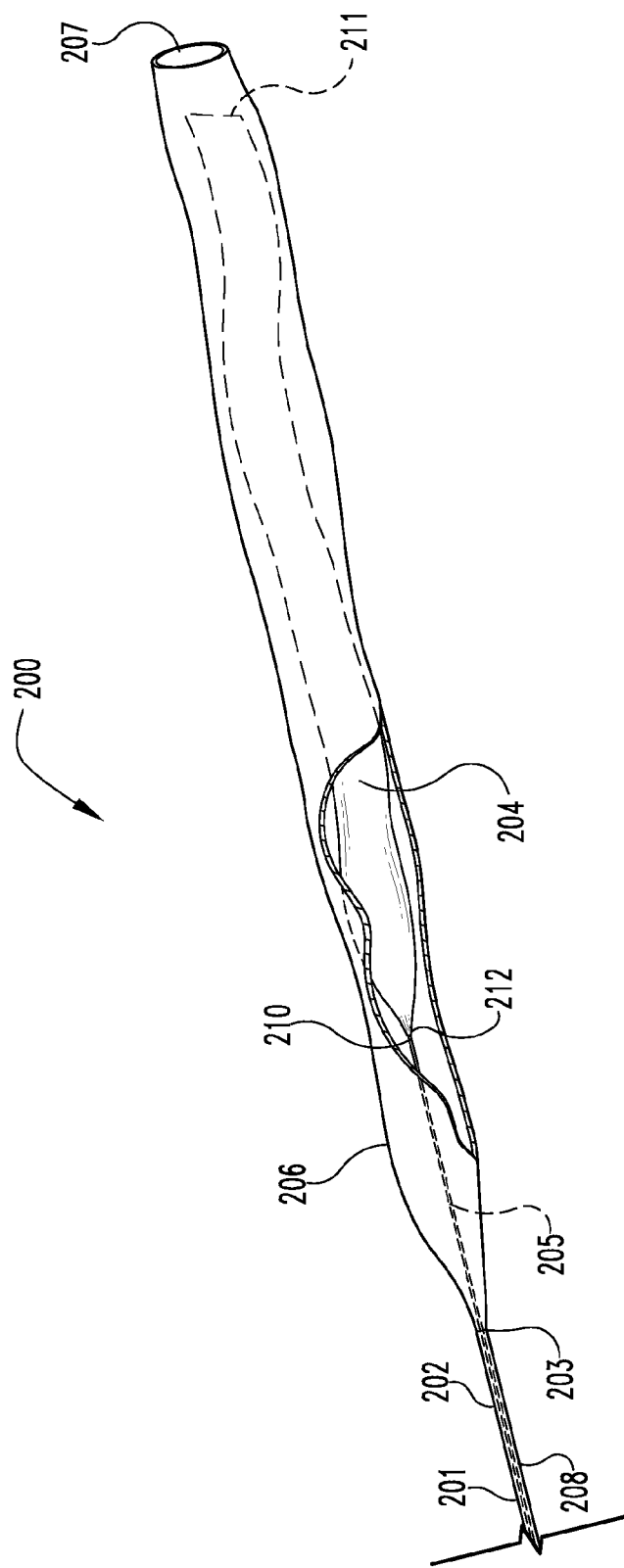
FIG. 8 is a perspective view of an alternative tissue augmentation device of the invention.

Referring now to FIG. 8, shown is a perspective view of an alternative tissue augmentation apparatus 200 of the present invention, which includes a needle 201, a segment of biocompatible implant material 204, and a flexible covering 206 surrounding the segment of material 204. This apparatus is similar to the one depicted in FIG. 1 in that it includes a needle 201 comprised of a cannulated, elongate portion 202 and a tapered portion (hidden in FIG. 8). The elongate portion 202 has a wall 208, a proximal end (hidden in FIG. 8), and a distal open end 203. Needle 201 further includes a proximal portion (hidden in FIG. 8) providing a tissue-penetrating device tip. In some aspects, material segment 204 comprises an angiogenic, remodelable collagenous biomaterial effective to promote patient tissue ingrowth into a region in which the biomaterial is implanted. The segment of material 204 has a leading end 212 and a trailing end 211. Additionally, apparatus 200 includes an attachment means 205 (e.g., a piece of suture material) which is useful in attaching the material segment 204 to needle 201. Apparatus 200 also includes a flexible covering 206 which has an open trailing end 207 and an open leading end 208 (hidden in FIG. 8). The open trailing end 207 can allow for access to the segment of material 204, such as to allow for rehydration or further sterilizing of the material. A portion of the flexible covering 206, including the covering's leading end 208, is received within the distal open end 203 of the elongate portion 202 to provide an internalized portion of the flexible covering 206.

In embodiments including a flexible covering, the segment of material 204 contained inside the covering can be indirectly attached to the needle and thus may or may not be received within the needle 201. In preferred embodiments, the flexible covering is secured directly to a portion of the needle 201 while the segment of material 204 is secured to the needle by an attachment means. A preferred attachment means is a suture. Referring again to FIG. 8, suture 205 has a leading end 209 (hidden in FIG. 8) and a trailing end 210. A portion of the suture 205 including its leading end 209 is received within the distal open needle end 203 and is secured in place. Accordingly, the illustrated attachment secures the segment of material to the needle indirectly while the flexible covering is secured to the needle directly.

The flexible covering can be made of any suitable flexible material. The flexible material can be selected from materials that can be easily maneuvered within tissue and that generally do not adhere to the segment of material that it covers. In preferred embodiments, the flexible material is a flexible, biocompatible plastic material. A variety of synthetic polymeric materials can be used to form a flexible covering, including but not limited to non-bioresorbable plastics. Non-bioresorbable, or biostable polymers that may be used include, but are not limited to, polytetrafluoroethylene (PTFE) (including expanded PTFE), polyethylene terephthalate (PET), polyurethanes, silicones, and polyesters and other polymers such as, but not limited to, polyolefins, polyisobutylene and ethylene-alphaolefin copolymers; acrylic polymers and copolymers, vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins, polycarbonates; polyoxymethylenes; polyimides; polyethers; epoxy resins, polyurethanes; rayon; and rayon-triacetate. In some forms of the invention, a flexible covering is comprised of a polymeric material that is generally impermeable to water and other fluids including biological fluids, while the tissue augmentation material selected for use is generally absorbent of water or biological fluids.

In some forms, the flexible covering material itself will be considered lubricious by those skilled in the art, while in other embodiments, these and other materials will include a layer (e.g., a coating) to enhance the lubricious properties of the covering. Such a layer may be applied (e.g., by spraying, dip coating, over-extruding or by any other suitable means) to the flexible covering and/or any other portion of the tissue augmentation device, and may be comprised of a hydrophilic material such as but not limited to parylene or PTFE. In certain aspects, UV (ultra-violet light)-curable, radiation-curable, photoreactive, photoimmobilizing, and other similar coatings are used. These coatings have in common at least one photoreactive species. Coatings can be made from these species, and then all or a portion of a tissue augmentation device can be coated and the coating cured. Lubricous coating materials include those commercially available from SurModics, Inc., Eden Prairie, Minn., under the trade mark "Photo-Link™."

Additionally or alternatively, the coating of the invention can incorporate an effective amount of one or more antimicrobial agents or therapeutic agents otherwise useful to inhibit the population of the tissue augmentation device or surrounding tissue with bacteria or other deleterious microorganisms. Illustrative such agents can include, for example, antibiotics such as penicillin, tetracycline, chloramphenicol, minocycline, doxycycline, vancomycin, bacitracin, kanamycin, neomycin, gentamycin, erythromycin and cephalosporins. Examples of cephalosporins include cephalothin, cephapirin, cefazolin, cephalexin, cephradine, cefadroxil, cefamandole, cefoxitin, cefaclor, cefuroxime, cefonicid, ceforanide, cefotaxime, moxalactam, ceftizoxime, ceftriaxone, and cefoperazone, and antiseptics (substances that prevent or arrest the growth or action of microorganisms, generally in a nonspecific fashion) such as silver sulfadiazine, chlorhexidine, glutaraldehyde, peracetic acid, sodium hypochlorite, phenols, phenolic compounds, iodophor compounds, quaternary ammonium compounds, and chlorine compounds. These or other therapeutic agents, can be incorporated directly on or in the protective covering material, or they can be incorporated with a suitable binder or carrier material, including for instance hydrogel materials. The carrier or binder coating can be applied to the flexible covering by any suitable means including, for example, spraying, dipping, etc. as known in the art. The antimicrobial or other therapeutic agent can be added to the carrier/binder coating either prior to or after application of the coating to the flexible material.

The tissue augmentation devices 20 and 200 depicted in FIGS. 1 and 8, respectively, are suitably configured to augment human facial tissue and in particular a human lip. Nonetheless, it should be understood that such a tissue augmentation device could be used and if need be adapted for any augmentation or restoration procedure, technique, situation, or patient. For example, the device 20 or 200 could be used to treat skin wrinkles, furrows, skin depressions, including depressed scars, nasal labial folds, and the like, as well as other tissue defects or deformations, e.g., those associated with aging, birth defects, accidents, trauma, etc.

The needle can be made of any suitable metal or other material. A plastically deformable metal such as stainless steel, e.g. type 304 stainless steel, can be used, and walls thereof can be plastically deformed by crimping or other methods to secure the segment of material within a cannulated portion. Other suitable metals include for example shape memory metals such as Nitinol or other shape memory nickel-titanium alloys. Such metals can also be plastically deformed; however, when using such shape memory metals, the thermally-induced shape memory effect can optionally be used in the securement of the segment of material alone or in addition to plastic deformation. For example, a cannulated portion of the needle can have first, non-constraining configuration (e.g. more open) at a temperature below its transition temperature, and a second, constraining configuration (e.g. more closed) at a temperature above its transition temperature, or vice versa. A portion of the segment of material can be passed into the cannulated portion while in the non-constraining configuration, and then the needle caused or allowed to proceed through its transition temperature thereby inducing a shape change of the cannula to its constraining configuration, and securing the segment of material. These and other modes of securing the segment of material at locations within cannulated portions of the needle will be apparent to those of ordinary skill in the art and utilizable in accordance with the present invention.

The illustrative segments of material 50 and 204 depicted in FIGS. 1 and 8, respectively, are generally rectangular, and can for example have a width of about 8 mm to about 12 mm, a length of about 14 cm to about 18 cm, and a thickness of about 0.05 mm (50 microns) to about 2 mm, although larger or smaller values for these dimensions could be used in accordance with the invention. The size, shape, and configuration of the device, or any component thereof, can be adapted to suit the requirements of any tissue augmentation or restoration procedure, technique, or patient. For example, in certain embodiments, a segment of material is a generally rectangular or other sheet form, and has a maximum width of about 1 mm to about 100 mm, more typically in the range of about 6 mm to about 15 mm, a length of about 1 cm to about 50 cm, more typically in the range of about 8 cm to about 20 cm, and a thickness in the range of about 0.1 mm to about 20 mm, more typically in the range of about 0.1 mm to about 4 mm. In still other embodiments, a segment of material comprises one or multiple more three dimensional structures such as braids, tubes, solid cylinders or hemi-cylinders of material, wherein such structures can have a length of about 1 cm to about 50 cm, more typically in the range of about 8 cm to about 20 cm, and a maximum cross-sectional dimension of about 1 mm to about 50 mm, more typically in the range of about 4 mm to about 16 mm.

In still further embodiments, the present invention provides segments of material that are circular, elliptical, or of any other suitable shape or cross-sectional geometry, or segments that comprise one or more strands, threads, strips, pieces, slabs, wedges, or blocks of material. In certain aspects, the size and shape of the segment of material is adapted to suit an unevenness or irregularity in the size and shape of a patient's lips, possibly resulting from a birth defect, accident, or trauma. In additional aspects, the segment of implantable material includes an elongate, resorbable sheet-form body wherein the body is highly pliable such that it is deformable from the sheet-form to a more three-dimensional form, such as a generally cylindrical form, upon impingement by soft tissues defining the tract formed by the needle or other tissue penetrating member. Such deformation of the sheet-form segment can occur by any suitable action, including for example rolling, gathering, folding, twisting, etc. of the sheet-form segment.

The present invention includes inventive embodiments wherein the sheet-form or other segment of implantable biomaterial has a maximum cross-sectional dimension that is substantially larger than that of the tissue penetrating member (e.g. needle). In particular aspects, the segment of implantable biomaterial can have a maximum cross-sectional dimension at least two times greater than that of the tissue penetrating element, e.g. in certain embodiments in the range of about three to about twenty times greater, more typically in the range of about three to about ten times greater. Also, in certain embodiments, the segment of implantable biomaterial has a length greater than that of the tissue penetrating member to which it is secured.

Implants useful in the present invention can be shaped and configured in a variety of manners. Inventive implants, in some forms, will include a biocompatible sheet-form material that is arranged to provide a volumetric body. Although not necessary to broader aspects of the invention, in certain aspects, such a volumetric body can be formed by folding, rolling, or otherwise overlaying one or more portions of a biocompatible sheet material. In some forms, an overlaid biocompatible sheet material is compressed and dried or otherwise bonded into a volumetric shape such that a substantially unitary construct is formed. Some of these volumetric bodies will include a fully or partially stabilized mass of collagenous material, for example, a mass that includes rolled and/or folded layers of a sheet-form collagenous extracellular matrix (ECM) material that have been dried under compression. In some preferred embodiments, an inventive implant, or a portion thereof, is formed with a remodelable, angiogenic material, for example, a sheet-form remodelable ECM material such as submucosa. These types of implants can be directly or indirectly secured or otherwise joined together with a tissue penetrating member in any suitable manner including any of those described herein. If the tissue penetrating member is equipped with an internal cannula, securement of the implant may involve receipt of the implant, or an intermediate material, in the cannula as described elsewhere herein.

Figure 11:
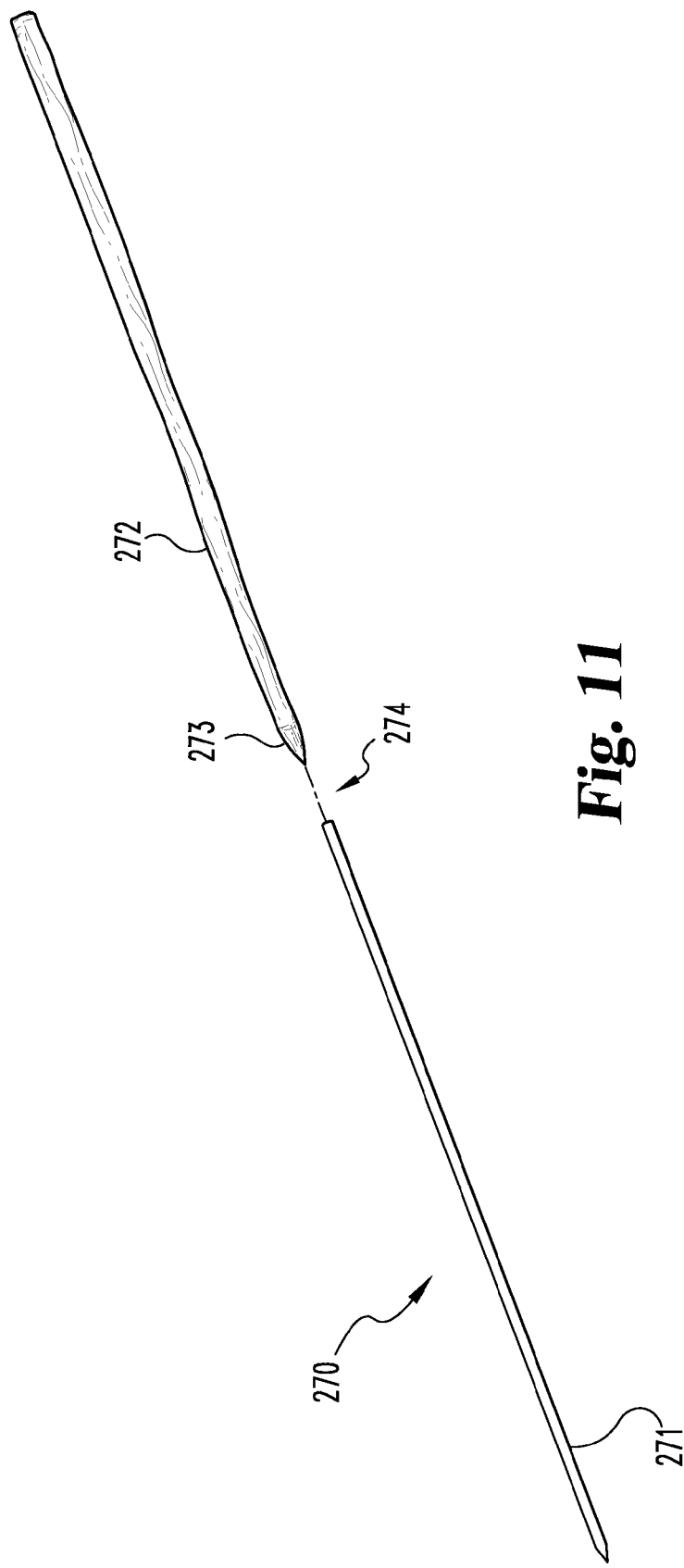
FIG. 11 is a perspective view of another tissue augmentation device of the invention.

With reference now to FIG. 11, shown is a tissue augmentation device 270 according to another embodiment of the present invention. Device 270 includes a tissue-penetrating member 271 and an implantable material 272. Implantable material 272 includes a rolled sheet-form material (e.g., a collagenous sheet material) that is formed into a generally cylindrical shape. This particular implant is shown having a leading tapered region 273, which is an optional feature. Tissue-penetrating member 271 and implantable material 272, in this specific illustrative embodiment, are connected together with an intermediate material 274. Shown in phantom in FIG. 11, this intermediate material can be a suture or other material capable of extending between and connecting tissue-penetrating member 271 to implantable material 272. An intermediate material of this sort can be secured to tissue-penetrating member 271 and implantable material 272 in any suitable manner including any of those described herein. Although not necessary to broader aspects of the invention, in embodiments where the intermediate material is a suture, this suture can be secured within an internal region of a tissue-penetrating member (if so equipped), and then also embedded within an implantable material, although other modes of attachment on either end are contemplated as well including some that involve use of adhesives, coupling devices and mechanisms, knot tying and combinations and variations thereof. An intermediate material can include an extension of the implant itself, this extension being suitably secured or otherwise joined to the tissue-penetrating member. In some forms, an intermediate material is excluded from the device, and a portion of the implantable material itself (e.g., a rolled or non-rolled sheet portion) is secured to the tissue-penetrating member, for example, as described elsewhere herein.

In certain aspects, formation of a volumetric body involves wrapping one or more material layers around a mandrel or otherwise applying material to a suitable supporting device such as a mold or form. Once wrapped fully around a device such as a mandrel, the outer edge of a layer can be fixed to an underlying wrapped portion. Additionally or alternatively, a thin layer of adhesive can be applied to each successive underlying layer as the construct is wrapped around a mandrel or other device, for example, so that a substantial portion of the rolled layers are adhered to one another. Any of these techniques may additionally or alternatively involve compression and drying steps.

When an inventive implant includes a rolled sheet-form material providing a volumetric body such as that shown in FIG. 11, this body may be in the shape of a cylinder, although other similarly formed graft bodies having non-cylindrical shapes can be constructed and used in the invention as well. When generally cylindrical, an implant body portion can, for example, have a diameter of about 0.5 mm to about 25.0 mm and a length of about 0.5 cm to about 30 cm, although larger or smaller values for these dimensions could be used in accordance with the invention. Thus, an implant in some forms of the invention will include a portion that is generally cylindrical, and has a diameter ranging from about 1.0 mm to about 8.0 mm, more typically from about 1.5 mm to about 4.0 mm, and a length ranging from about 2.0 cm to about 18.0 cm, more typically from about 4.0 cm to about 12.0 cm. As well, an implant body portion such as that shown in FIG. 11 may be formed with one or more of a variety of biocompatible materials including some that are naturally derived and some that are non-naturally derived.

An implant body can have a constant or varying cross-sectional area along its length. Illustratively, an implant body, or any portion thereof, can exhibit a generally cylindrical shape, a conical shape or any other suitable shape including some that have tapered and/or non-tapered longitudinal portions. As well, a cross section of a particular portion of an implant body can exhibit a variety shapes including some that have rectilinear and/or curvilinear features. Thus, an implant body can include a portion having a generally circular or non-circular (e.g., elliptical, square, star-shaped, hexagonal, etc.) cross section.

The implant bodies and other implant components described herein can be formed in any suitable manner including but not limited to by extrusion, using a mold or form, construction around a mandrel, and/or combinations or variations thereof. In some embodiments, an implant body is formed with a reconstituted or otherwise reassembled ECM material. Implant bodies can also be formed by folding or rolling, or otherwise overlaying one or more portions of a biocompatible material, such as a biocompatible sheet material. The overlaid biocompatible sheet material can be compressed and dried or otherwise bonded into a volumetric shape such that a substantially unitary construct is formed. In some forms, an inventive implant component is constructed by randomly or regularly packing one or more pieces of single or multilayer ECM sheet material within a mold and thereafter processing the packed material.

Methods for forming implant bodies useful in the invention can involve manipulating a material within a mold or form. It should be noted that this material may or may not be hydrated when placed in, on, around, etc. the mold or form. In some methods, a substantially dry ECM material (e.g., a powder or sheet material) can be placed in a mold and then suitably hydrated for further processing. In other methods, a hydrated starting material is placed in and/or on a mold or forming structure for further processing. For example, one or more hydrated sheets of ECM material can be applied to a form, e.g., wrapped at least partially around a mandrel so that portions of the sheet(s) overlap. Then, the one or more sheets can be dried, and in some embodiments, dried while under compression, to form a unitary implant body.

In some modes of formation, a hydrated graft material is provided within a single- or multiple-part mold having a plurality of apertures or holes extending through a wall of the mold, thereby providing access to the mold interior from an external location. These apertures can serve to enhance drying of a hydrated material during a processing step and in processes exerting vacuum pressure at these apertures, can promote and/or facilitate formation of surface protuberances on the graft material as portions of the same are drawn toward the apertures while under vacuum. In one aspect, an amount of ECM material is retained in such a mold, and needles or other material-displacing objects are inserted through some or all of the mold apertures and a distance into the ECM material, thereby displacing volumes of the ECM material. This can be performed when the graft material is hydrated, partially hydrated or dehydrated. In some forms, with needles inserted in a hydrated ECM material and providing passages therein, the material is subjected to conditions (e.g., freezing and/or dehydrating conditions) which, alone or in combination with one or more other conditions, cause or allow the passages to be generally retained in the ECM material after the needles are removed.

In one embodiment, one or more sheets of hydrated ECM material are suitably wrapped and/or randomly packed around a mandrel, and then a mold having a plurality of holes extending through a wall of the mold is placed around the material-covered mandrel, for example, so that an amount of pressure is placed on the ECM material. The mandrel can then optionally be removed. Thereafter, needles or other material-displacing objects are inserted through some or all of the holes and at least partially through the ECM material, thereby displacing volumes of the ECM material. The ECM material is then at least partially dried. In some aspects, a suitable lyophilization technique is employed, e.g., one with or without a pre-freezing step as described herein. In these or other drying methods in which needles or other penetrating elements are to be left within the mass during drying, these elements can optionally be provided with a plurality of apertures or holes or can otherwise be sufficiently porous to facilitate the drying operation by allowing the passage of hydrate from the wet mass. In one embodiment, a hydrated ECM material with emplaced needles can be subjected to freezing conditions so that the material and any contained hydrate become substantially frozen. Thereafter, the needles can be removed from the ECM material, and the remaining construct (with the frozen material passages substantially retaining their shape) can be placed under a vacuum so that the frozen hydrant sublimes from the material, thereby resulting in a dry implant body with retained passages therein.

In other modes of operation, passage-forming structures can be incorporated integrally into a mold so that passageways are formed upon introducing the starting material in and/or on the mold. In these aspects, the passage-forming structures can be part of the mold (e.g., extend from a surface of the mold), or they can be separate objects attached or otherwise coupled to the mold, to provide the desired passage or passages through the ultimately-formed implant body.

Although not necessary to broader aspects of the invention, in some aspects, the formation of such an implant body comprises wrapping one or more sheets of hydrated graft material around a mandrel a number of times. The resulting roll of graft material is then introduced into a mold, and the mandrel is removed (optional), e.g., before or after applying the mold. Thereafter, multiple material-displacing objects such as but not limited to needles are forced through apertures in the mold and into the hydrated graft material, and the material is subjected to one or more drying techniques such as a lyophilization process. In other aspects, the formation of such an implant body includes placing a flowable graft material into a mold and then subjecting the graft material to further processing. For example, a flowable ECM material mass, such as a gel, paste or putty, potentially incorporating a particulate ECM material, can be placed into a mold, and then with volumes of material displaced in the mass (e.g., by penetrating needles), the ECM material can be dried or otherwise caused to form an integral piece to provide an implant body having passages therein. Illustratively, each of the passages can be provided by forcing a single object through the material mass, or alternatively, where a mandrel is left in place to form a longitudinal lumen, by forcing two objects into the mass and toward one another from opposite directions until they abut the mandrel. The mass can then be processed to a solid implant body as discussed herein.

In certain forms of the invention, a sheet-form or non-sheet segment of implantable material will be particularly adapted so that its shape and/or size can be readily altered before and/or during an implantation procedure. These types of implants can be altered in one dimension, or in more than one dimension, and can exhibit a variety of shapes and sizes both before and after an alteration is performed. Alterable dimensions include length, width, thickness, diameter, and combinations and variations thereof. An alteration may involve removing and discarding one or more parts of an implant that are specifically identifiable as being removable. In some preferred embodiments, a customizable implant has a measurable size, volume, etc., and this measured figure can be quickly and easily reduced by a predetermined amount by removing a portion of the implant prior to implantation. For example, an implant body can have an initial volume V1, and by removing one or more pre-identified portions of this body, volume V1 can be reduced by up to 90% or more, and more commonly reduced by about 1% to about 80%, and even more commonly reduced by about 10% to about 60%. Illustratively, an implant initially in the form of an elongated strip or other segment can incorporate one or more adaptations to facilitate a reduction in its width, diameter, etc. along all or part of its length prior to implantation. In this regard, inventive implants can be adapted to suit a wide variety of implant scenarios. Some inventive implants will be constructed having a generic first set of dimensions, yet will provide options for quickly and easily obtaining one or more alternative sets of dimensions prior to implantation, for example, by allowing the length and/or width of the implant to be changed just prior to being implanted.

In some forms, an implant will incorporate one or more adaptations for facilitating separation of one implant segment from another before and/or during an implant procedure. Illustratively, an implant can incorporate scores, thinner portions, and other openings and non-openings that weaken structurally a portion of the implant to facilitate a tear-away operation or cutting therealong with scissors, scalpel, etc. in removing one part of the implant from another. Such a weakened portion may include any suitable means for facilitating tearing, cutting or breaking along the area. In certain beneficial forms, an implant is controllably separable along a particular grouping of weakened portions in the implant, e.g., along a plurality of weakened portions forming a generally straight or curved line. These types of adaptations can be incorporated into an implant in a variety of ways as will be appreciated by those skilled in the art. Illustratively, a sheet-form or other type of implant segment, in certain embodiments, can be originally formed (e.g., in a mold, extruded, etc.) with weakened portions already incorporated into the construct. When formed in an existing material (e.g., a harvested collagen-containing material sheet), weakened portions or other similar adaptations can be formed using a variety of techniques and instruments, for example, using lasers such as in laser etching, or employing any number of other tools or instruments. Forming these types of adaptations may or may not involve removing or otherwise eliminating portions of the implant material.

Figure 12:
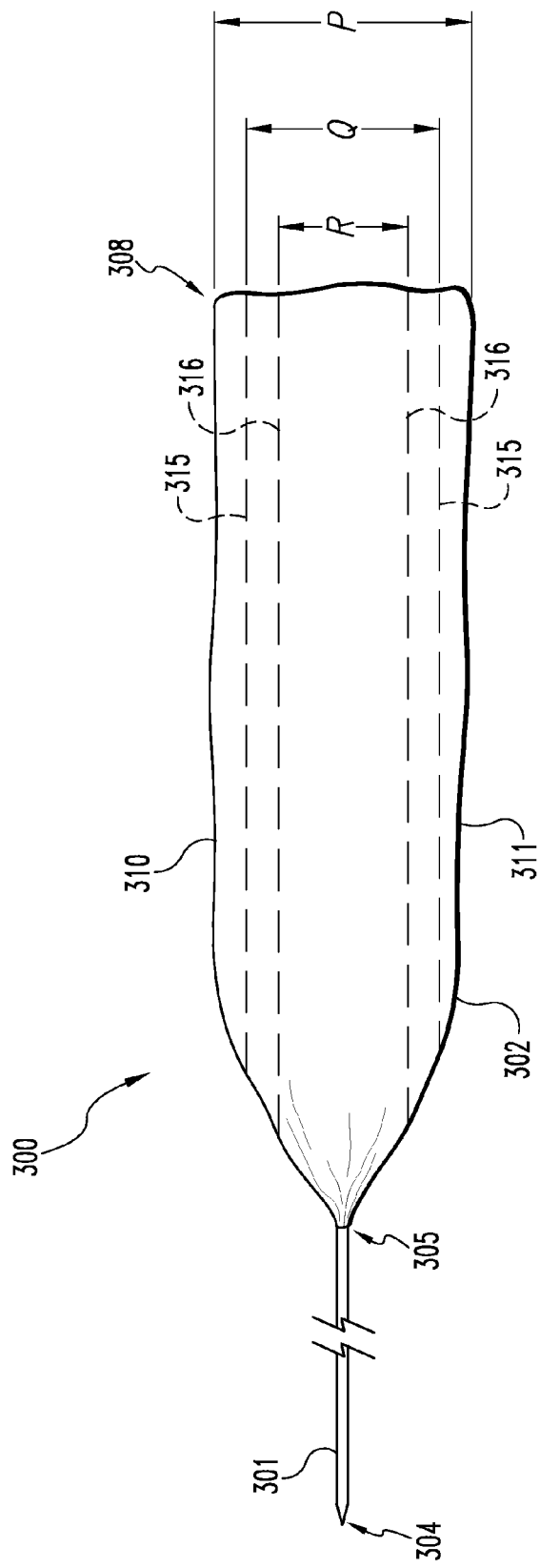
FIG. 12 is a top view of yet another tissue augmentation device of the invention.

With reference now to FIG. 12, shown is a top view of another tissue augmentation device 300 of the present invention. Device 300 includes a tissue-penetrating member 301, and a sheet-form segment of biocompatible implant material 302. These two components are secured to one another in such a way that advancing tissue-penetrating member 301 through tissue is effective to also advance implant material 302 through the same tissue. Implant material 302 and tissue-penetrating member 301 can be secured or otherwise joined together in any suitable manner including some that involve use of an adhesive and/or a coupling device or mechanism, or otherwise in accordance with the other modes of attachment described herein. As will be recognized by the skilled artisan, any of these attachment modes can be used in constructing the various tissue augmentation devices of the invention. As shown, tissue-penetrating member 301 is at least partially cannulated, and includes a tissue-penetrating tip 304 on one end and an opening 305 in communication with an internal cannula on its opposite end. A portion of implant material 302 is received in the internal cannula through opening 305, causing portions of the material in and around opening 305 to become gathered or bunched up, as shown.

A segment of material such as that shown in FIG. 12 can be shaped and configured in a variety of manners. In this specific illustrative embodiment, implant material 302 is generally rectangular in shape. It has a leading end (hidden), which is positioned inside the internal cannula, and a trailing end 308. Implant material 302 also has a first side 310 and a second side 311, the distance between these sides providing an overall width, P, as depicted in FIG. 12. Multiple rows of perforations are formed in a longitudinal direction along sheet 302 so that, if desired, the width of the sheet can be adjusted prior to an implantation procedure. Material can be separated along any of the perforation lines shown. If material is separated along a first set of perforation rows 315, the remaining sheet will have a corresponding width, Q, as shown in FIG. 12. If material is separated along a second set of perforation rows 316, the remaining sheet will have a corresponding width, R, as shown. In this way, a single device can be altered to suit a wide range of implant scenarios.

In one preferred embodiment, a sheet-form implantable material has an initial width, P, of about 0.5 cm to about 10 cm, more typically about 1 cm to about 5 cm, and even more typically from about 1.5 cm to about 3 cm. First set of perforation rows 315 can be located on the sheet such that by separating material along these perforations as described above, the remaining implant will have a width Q that is about 10% to about 70% less than initial width P, more typically about 10% to about 40% less than initial width P, and even more typically about 20% to about 30% less then initial width P. Second set of perforation rows 316 can be located on the sheet such that by separating material along these perforations as described above, the remaining implant will have a width R that is about 10% to about 70% less than width Q, more typically about 10% to about 40% less than width Q, and even more typically about 20% to about 30% less than width Q. When rows of perforations (or other organized groupings of weakened portions) are incorporated into an implant, the implant can have more or less rows than what is shown in FIG. 12. Also, perforations or other weakened portions can be formed in a straight line, or can exhibit any number of other shapes having rectilinear and/or curvilinear features, as desired. Although not necessary to broader aspects of the invention, in certain embodiments, weakened portions of this sort and other adaptations for facilitating separation of one implant segment from another will be formed in an implant before combining the implant material and the tissue penetrating member.

The materials used in the present invention should generally be biocompatible. In certain embodiments, a tissue augmentation device is comprised of a tissue ingrowth-receptive material. Such devices may be formed with one or more of a variety of suitable tissue ingrowth materials including reconstituted and naturally-derived collagenous materials. In some aspects of the invention, such materials that are bioremodelable and promote cellular invasion and ingrowth will provide particular advantage. For example, suitable bioremodelable materials can be provided by collagenous extracellular matrix materials (ECMs) possessing biotropic properties, including in certain forms angiogenic collagenous extracellular matrix materials.

In certain forms of the invention, the segment of material is formed with a generally biocompatible extracellular matrix (ECM) material, which can be a remodelable ECM material that promotes patient tissue ingrowth. Suitable ECM material for use in the present invention can be derived from a variety of natural sources, including pericardial tissues (e.g., pericardial sacs), amniotic membranes, connective tissues, dermal tissue (including but not limited to cadaveric human or porcine dermal tissue), blood vessels, cartilage, dura mater, fascia, umbilical tissues, renal capsule membrane, serosa, peritoneum, basement membrane materials (e.g., liver basement membrane), submucosa and the like. ECM materials can be derived from a particular animal species, typically mammalian, such as human, bovine, equine, ovine, or porcine. These materials may include a portion of an organ or structural tissue components of an organ. Moreover, suitable remodelable tissues include xenografts (i.e., cross species, such as a non-human donor for a human recipient), allografts (i.e., interspecies with a donor of the same species as the recipient) and autografts (i.e., the donor and the recipient being the same individual). Suitable ECM materials for use in the present invention are also commercially available and include for example products known as Surgisis (an acellular porcine small intestine submucosa product, Cook Biotech Incorporated), AlloDerm (an acellular human cadaveric dermal product, LifeCell Corp.), Tutoplast (a processed facia lata product, Mentor Corporation), Permacol (an acellular porcine dermal collagen product, from Tissue Science Laboratories), Pelvicol (an acellular porcine dermal collagen product, Bard Inc.), and Peri-Guard and Veritas (acellular bovine pericardium products, Synovis Life Technologies, Inc.). In certain embodiments, the ECM material is additionally crosslinked as discussed in below, while in other embodiments the ECM material substantially retains its native level of crosslinking.

Submucosal tissue obtained from cattle, sheep, and other warm-blooded vertebrates, especially pigs, provides a particularly preferred material for use in the present invention. A favorable characteristic of remodelable submucosal tissue (e.g., small intestinal submucosa, stomach submucosa, urinary bladder submucosa, or uterine submucosa) is that it has the capacity to induce host tissue proliferation and lead to the remodeling and regeneration of tissue structures upon in vivo implantation. Accordingly, submucosal tissue is particularly suitable for forming the segment of material, since it is desirable to promote tissue ingrowth into the segment from the implantation site.

The ECM materials processed for use in the invention will typically include abundant collagen, most commonly being constituted at least about 80% by weight collagen on a dry weight basis. Such naturally-derived ECM materials will for the most part include collagen fibers that are non-randomly oriented, for instance occurring as generally uniaxial or multi-axial but regularly oriented fibers. When processed to retain native bioactive factors, the ECM material can retain these factors interspersed as solids between, upon and/or within the collagen fibers. Particularly desirable naturally-derived ECM materials for use in the invention will include significant amounts of such interspersed, non-collagenous solids that are readily ascertainable under light microscopic examination with appropriate staining. Such non-collagenous solids can constitute a significant percentage of the dry weight of the ECM material in certain inventive embodiments, for example at least about 1%, at least about 3%, and at least about 5% by weight in various embodiments of the invention.

The submucosa or other ECM material used in the present invention may also exhibit an angiogenic character and thus be effective to induce angiogenesis in a host engrafted with the material. In this regard, angiogenesis is the process through which the body makes new blood vessels to generate increased blood supply to tissues. Thus, angiogenic materials, when contacted with host tissues, promote or encourage the formation of new blood vessels into the materials. Methods for measuring in vivo angiogenesis in response to biomaterial implantation have recently been developed. For example, one such method uses a subcutaneous implant model to determine the angiogenic character of a material. See, C. Heeschen et al., *Nature Medicine* 7 (2001), No. 7, 833-839. When combined with a fluorescence microangiography technique, this model can provide both quantitative and qualitative measures of angiogenesis into biomaterials. C. Johnson et al., *Circulation Research* 94 (2004), No. 2, 262-268.

Submucosal or other ECM tissue may, for example, be prepared as described in U.S. Pat. Nos. 4,902,508; 5,554,389; and 6,206,931. Again, it should be understood that submucosa or other ECM material can be derived from any suitable organ or other biological structure, including for example, from the alimentary, respiratory, intestinal, urinary or genital tracts of warm-blooded vertebrates. Submucosa or other ECM material useful in the present invention can be obtained by harvesting such tissue sources and delaminating the submucosa/ECM from smooth muscle layers, mucosal layers, and/or other layers occurring in the tissue source. Thereafter, the submucosa/ECM can be assembled into tissue segments (e.g., sheets, strands, and other shapes) or stored for later processing.

In certain aspects of the invention, the segment may also be formed with biological or synthetic polymers, resorbable or non-resorbable. Biological polymers, for instance, can be derived from naturally occurring tissues or the product of in vitro fermentation, recombinant genetic engineering, and the like. Suitable biological polymers include, without limitation, collagen, elastin, keratin, gelatin, polyamino acids, polysaccharides (e.g., cellulose and starch) and copolymers thereof. Polymers can be suitably formed into an implant segment material by techniques such as weaving, knitting, casting, molding, and/or extrusion.

Crosslinking, in addition to providing mechanical stabilization (e.g., by anchoring the collagen fibrils and preventing enzymatic degradation of the tissue), can decrease or eliminate antigens in ECM material used in the invention. Glutaraldehyde, formaldehyde or a combination thereof is typically used for fixation, but other fixatives can be used, such as epoxides, epoxyamines, diimides and other difunctional/polyfunctional aldehydes. In particular, aldehyde functional groups are highly reactive with amine groups in proteins, such as collagen. Epoxyamines are molecules that generally include both an amine moiety (e.g. a primary, secondary, tertiary, or quaternary amine) and an epoxide moiety. The epoxyamine compound can be a monoepoxyamine compound and/or a polyepoxyamine compound.

In addition to potentially being crosslinked, the ECM material can potentially be treated (e.g., brought into contact, impregnated, coated, etc.) with one or more desirable compositions, such as anticoagulants (e.g., heparin), growth factors, other desirable property modifiers, and the like to modify the tissue properties. Specifically, the tissue can be treated with an anticalcification agent to reduce calcification of the tissue following implantation and/or to encourage tissue remodeling. In certain embodiments, a calcification reducing agent is contacted with the material before or after crosslinking. Suitable calcification reducing agents include, for example, alcohols, such as ethanol and propylene glycol, detergents (e.g., sodium dodecyl sulfate), toluidine blue, diphosphonates, and multivalent cations, especially $Al^{+3}$, $Mg^{+2}$ or $Fe^{+3}$, or corresponding metals that can oxidize to form the multivalent metal cations.

Additionally, to encourage ingrowth of viable cells, aldehyde-crosslinked ECM materials can be treated to reduce or eliminate toxicity associated with aldehyde crosslinking and/or associated with compounds that stimulate the infiltration of the tissue by desirable cells. Further, the ECM material can be crosslinked with dialdehydes or the like to reduce or eliminate any cytotoxicity. Suitable compounds for reduction of aldehyde cytotoxicity include, for example, amines, such as amino acids, ammonia/ammonium, sulfates, such as thiosulfates and bisulfates, surfactants and combinations thereof.

As prepared, ECM material used in the present invention may optionally retain various bioactive components native to the source tissue. For example, the ECM material may include one or more growth factors, such as basic fibroblast growth factor (FGF-2), transforming growth factor beta (TGF-beta), epidermal growth factor (EGF), cartilage derived growth factor (CDGF) and/or platelet derived growth factor (PDGF). Further, submucosa or other ECM material used in the present invention may include other biological substances, such as heparin, heparin sulfate, hyaluronic acid, fibronectin and the like. Thus, generally speaking, an ECM material used in the present invention may include a bioactive component that induces, directly or indirectly, a cellular response, such as a change in cell morphology, proliferation, growth, protein or gene expression, which again, is desirable for promoting tissue ingrowth into the segment of material from the implantation site.

In addition to, or as an alternative to, the inclusion of such native bioactive components, non-native bioactive components, such as those synthetically produced by recombinant technology or other methods, may be incorporated into an ECM material used in the invention. The addition of a non-native component, e.g., a growth factor, with a tissue matrix may involve direct attachment, application of a coating, including an adhesive or binder, or chemical binding, involving a binding agent.

ECM material, when used in the present invention, is preferably highly purified and can for example be prepared and/or have the characteristics as described in U.S. Pat. No. 6,206,931. Thus, the preferred material will exhibit an endotoxin level of less than about 12 endotoxin units (EU) per gram, more preferably less than about 5 EU per gram, and most preferably less than about 1 EU per gram. As additional preferences, the ECM material may have a bioburden of less than about 1 colony forming units (CFU) per gram, and more preferably less than about 0.5 CFU per gram. Fungus levels are desirably low as well, for example less than about 1 CFU per gram, and more preferably less than about 0.5 CFU per gram. Nucleic acid levels are preferably less than about 5 μg/mg, and more preferably less than about 2 μg/mg, while virus levels are preferably less than about 50 plate forming units (PFU) per gram, and more preferably less than about 5 PFU per gram. These and additional properties of submucosa or other ECM materials taught in U.S. Pat. No. 6,206,931 may be characteristic of the ECM material used in the present invention.

The implant material segment can be provided by a single layer of material or a multilaminate construct. Thus, in certain embodiments, a single isolated layer of ECM material or a multilaminate ECM construct can be used. Illustrative multilaminate ECM constructs for use in the invention may, for example, have from two to about ten isolated ECM layers laminated together. Whether single layer or multilayer ECM materials are used, the overall layer thickness of an ECM-containing segment can for example be from about 50 microns to about 1500 microns when fully hydrated, typically ranging from about 100 to about 1000 microns, more typically from about 100 to about 500 microns.

The layer thickness for an isolated single submucosal or other ECM layer can, in certain embodiments, range from about 50 to about 500 microns when fully hydrated, advantageously about 100 to about 300 microns. As noted above, these isolated ECM layers can be used either alone or in multilayer constructs to provide implant segment. It will be understood, however, that these and the other ECM layer thicknesses discussed herein may vary with the particular ECM tissue isolated, the type and age or size of the animal used as the tissue source, or other factors.

Multilaminate ECM constructs for use in the invention can be prepared in any suitable fashion. In this regard, a variety of techniques for laminating ECM layers together can be used. These include, for instance, dehydrothermal bonding under heated, non-heated or lyophilization conditions, using adhesives, glues or other bonding agents, crosslinking with chemical agents or radiation (including UV radiation), or any combination of these with each other or other suitable methods. For additional information as to multilaminate ECM constructs that can be used in the invention, and methods for their preparation, reference may be made for example to U.S. Pat. Nos. 5,711,969, 5,755,791, 5,855,619, 5,955,110, 5,968,096, and to U.S. Patent Publication No. 20050049638 A1 published Mar. 3, 2005.

Single layer ECM or multilaminate ECM constructs or other biocompatible implant segments used in the present invention can have or can lack perforations or slits in their structure, and in certain embodiments can have a meshed structure for example as described in United States Patent Publication No. 20050021141 dated Jan. 27, 2005 and entitled Medical Graft Device With Meshed Structure, which is incorporated herein by reference. Such mesh patterned structures can be used provide an ECM or other implant segment that is highly deformable for use in the present invention.

In additional embodiments, medical graft products of the invention can be made from ECM's or other collagenous materials that have been subjected to processes that expand the materials. In certain forms, such expanded materials can be formed by the controlled contact of an ECM material with one or more alkaline substances until the material expands, and the isolation of the expanded material. Illustratively, the contacting can be sufficient to expand the ECM material to at least 120% of (i.e. 1.2 times) its original bulk volume, or in some forms to at least about two times its original volume. Thereafter, the expanded material can optionally be isolated from the alkaline medium, e.g. by neutralization and/or rinsing. The collected, expanded material can be used in any suitable manner in the preparation of a graft device. Illustratively, the expanded material can be enriched with bioactive components, dried, and/or molded, etc., in the formation of a graft construct to a desired shape or configuration. In certain embodiments, a dried graft construct formed with the expanded ECM material can be highly compressible (or expandable) such that the material can be compressed for delivery, such as from within the lumen of a cannulated delivery device, and thereafter expand upon deployment from the device so as to become anchored within a patient and/or cause closure of a tract within the patient.

Expanded collagenous or ECM materials can be formed by the controlled contact of a collagenous or ECM material with an aqueous solution or other medium containing sodium hydroxide. Alkaline treatment of the material can cause changes in the physical structure of the material that in turn cause it to expand. Such changes may include denaturation of the collagen in the material. In certain embodiments, it is preferred to expand the material to at least about three, at least about four, at least about 5, or at least about 6 or even more times its original bulk volume. The magnitude of the expansion is related to several factors, including for instance the concentration or pH of the alkaline medium, exposure time, and temperature used in the treatment of the material to be expanded.

ECM materials that can be processed to make expanded materials can include any of those disclosed herein or other suitable ECM'S. Typical such ECM materials will include a network of collagen fibrils having naturally-occurring intramolecular cross links and naturally-occurring intermolecular cross links. Upon expansion processing as described herein, the naturally-occurring intramolecular cross links and naturally-occurring intermolecular cross links can be retained in the processed collagenous matrix material sufficiently to maintain the collagenous matrix material as an intact collagenous sheet material; however, collagen fibrils in the collagenous sheet material can be denatured, and the collagenous sheet material can have an alkaline-processed thickness that is greater than the thickness of the starting material, for example at least 120% of the original thickness, or at least twice the original thickness.

Illustratively, the concentration of the alkaline substance for treatment of the remodelable material can be in the range of about 0.5 M to about 4 M, with a concentration of about 1 M to about 3 M being more preferable. Additionally, the pH of the alkaline substance can in certain embodiments range from about 8 to about 14. In preferred aspects, the alkaline substance will have a pH of from about 10 to about 14, and most preferably of from about 12 to about 14.

In addition to concentration and pH, other factors such as temperature and exposure time will contribute to the extent of expansion, as discussed above. In this respect, in certain variants, the exposure of the collagenous material to the alkaline substance is performed at a temperature of about 4 to about 45° C. In preferred embodiments, the exposure is performed at a temperature of about 25 to about 40° C., with 37° C. being most preferred. Moreover, the exposure time can range from at least about one minute up to about 5 hours or more. In some embodiments, the exposure time is about 1 to about 2 hours. In a particularly preferred embodiment, the collagenous material is exposed to a 1 M solution of NaOH having a pH of 14 at a temperature of about 37° C. for about 1.5 to 2 hours. Such treatment results in collagen denaturation and a substantial expansion of the remodelable material. Denaturation of the collagen matrix of the material can be observed as a change in the collagen packing characteristics of the material, for example a substantial disruption of a tightly bound collagenous network of the starting material. A non-expanded ECM or other collagenous material can have a tightly bound collagenous network presenting a substantially uniform, continuous surface when viewed by the naked eye or under moderate magnification, e.g. 100× magnification. Conversely, an expanded collagenous material can have a surface that is quite different, in that the surface is not continuous but rather presents collagen strands or bundles in many regions that are separated by substantial gaps in material between the strands or bundles when viewed under the same magnification, e.g. about 100×. Consequently, an expanded collagenous material typically appears more porous than a corresponding non-expanded collagenous material. Moreover, in many instances, the expanded collagenous material can be demonstrated as having increased porosity, e.g. by measuring for an increased permeability to water or other fluid passage as compared to the non-treated starting material. The more foamy and porous structure of an expanded ECM or other collagenous material can allow the material to be cast or otherwise prepared into a variety of sponge or foam shapes for use in the preparation of medical materials and devices. It can further allow for the preparation of constructs that are highly compressible and which expand after compression. Such properties can be useful, for example, when the prepared graft construct is to be compressed and loaded into a deployment device (e.g. a lumen thereof) for delivery into a patient, and thereafter deployed to expand at the implant site.

After such alkaline treatments, the material can be isolated from the alkaline medium and processed for further use. Illustratively, the collected material can be neutralized and/or rinsed with water to remove the alkalinity from the material, prior to further processing of the material to form a graft construct.

A starting ECM material (i.e., prior to treatment with the alkaline substance) can optionally include a variety of bioactive or other non-collagenous components including, for example, growth factors, glycoproteins, glycosaminoglycans, proteoglycans, nucleic acids, and lipids. Treating the material with an alkaline substance may reduce the quantity of one, some or all of such non-collagenous components contained within the material. In certain embodiments, controlled treatment of the remodelable material with an alkaline substance will be sufficient to create a remodelable collagenous material which is substantially devoid of nucleic acids and lipids, and potentially also of growth factors, glycoproteins, glycosaminoglycans, and proteoglycans.

In certain embodiments, one or more bioactive components, exogenous or endogenous, for example, similar to those removed from an expanded material during alkaline processing, can be returned to the material. For example, an expanded material can include a collagenous material which has been depleted of nucleic acids and lipids, but which has been replenished with growth factors, glycoproteins, glycosaminoglycans, and/or proteoglycans. These bioactive components can be returned to the material by any suitable method. For instance, in certain forms a tissue extract, such as is discussed in U.S. Pat. No. 6,375,989 which is hereby incorporated herein by reference in its entirety, containing these components can be prepared and applied to an expanded collagenous material. In one embodiment, the expanded collagenous material can be incubated in a tissue extract for a sufficient time to allow bioactive components contained therein to associate with the expanded collagenous material. The tissue extract may, for example, be obtained from non-expanded collagenous tissue of the same type used to prepare the expanded material. Other means for returning or introducing bioactive components to an expanded remodelable collagenous material include spraying, impregnating, dipping, etc. as known in the art. By way of example, an expanded collagenous material may be modified by the addition of one or more growth factors such as basic fibroblast growth factor (FGF-2), transforming growth factor beta (TGF beta), epidermal growth factor (EGF), platelet derived growth factor (PDGF), and/or cartilage derived growth factor (CDGF). As well, other biological components may be added to an expanded collagenous material, such as heparin, heparin sulfate, hyaluronic acid, fibronectin and the like. Thus, generally speaking, an expanded collagenous material may include a bioactive component that induces, directly or indirectly, a cellular response such as a change in cell morphology, proliferation, growth, protein or gene expression similar to a non-expanded collagenous material.

Expanded collagenous materials can be used to prepare a wide variety of tissue augmentation devices. Methods for preparing such plug devices can include contacting an ECM or other collagenous starting material with an alkaline substance in an amount effective to expand the material, casting or otherwise forming the expanded collagenous material into a plug shape (e.g. one of those described herein), and lyophilizing the expanded material to form a dried plug device.

Referring now again to the drawings, FIG. 2 provides a partial, top view of the tissue augmentation device 20 of FIG. 1, highlighting an area of the needle 30 proximate the distal end 35 of the elongate portion 31. In this region, the needle 30 has a slot 70, a first hole 71, and a second hole 72, all of which are defined in the wall 33 of the elongate portion 31. Such slots and holes may be machined or otherwise processed into the needle using known techniques, including for instance electrical discharge machining (EDM). Further, the slot 70, first hole 71, and second hole 72 are located and aligned on one side of the needle 30, along a substantially straight line C running from the proximal end 34 to the distal end 35 of the elongate portion 31. The slot 70 has a first end 73 and a second end 74. The slot 70 is configured to receive an instrument therethrough to help draw the segment of material 50 into the needle 30 during the manufacture of the tissue augmentation device 20. The first hole 71 and second hole 72 are positioned between the slot 70 and the distal end 35, and are configured to receive a sterilizing agent therethrough.

In one illustrative embodiment, the slot 70 is approximately 0.635 mm (about 0.025 inches) wide, the first end 73 of the slot 70 is approximately 12-13 mm (e.g. about 0.5 inches) from the distal end 35 of the elongate portion 31, the second slot end 74 is approximately 18-20 mm (e.g. about 0.75 inches) from the distal end 35, the first hole 71 and second hole 72 each have a diameter of approximately 0.4 mm (e.g. about 0.015 inches) and are located along the substantially straight line C running from the proximal end 34 to the distal end 35 of the elongate portion 31. As well, in such an illustrative embodiment, the center of the first hole 71 can be located approximately 5 mm (e.g. about 0.195 inches) from the distal end 35 of the elongate portion 31, while the center of the second hole 72 is located approximately 5 mm (e.g. about 0.195 inches) from the center of the first hole 71. It will be understood that this embodiment is described for purposes of illustrating one possible manner of carrying out the invention and is not restrictive of the broader aspects of the invention. Thus, the dimensions of the slot 70, first hole 71, and second hole 72, as well as their location and orientation on the needle 30, can vary. Also, it should be understood that present invention provides tissue augmentation device 20 embodiments not having a slot 70, a first hole 71, and/or a second hole 72. Further, any slot need not be rectangular, and any hole need not be circular. Openings of any suitable size, shape, and configuration are contemplated as within the scope of the present invention.

Continuing with FIG. 2, the needle 30 provides a plurality of deformed regions 60 proximate the distal end 35 of the elongate portion 31. The deformations 60 are configured to constrict portions of the segment of material 50 received within the needle 30. During one illustrative tissue augmentation device 20 manufacturing process (an example of which is described below in relation to FIG. 4), the leading end 51 of the segment of material 50 can be drawn into the needle 30 in a gathered configuration (e.g. rolled, folded and/or twisted) until it reaches a desired point within the elongate portion 31 (represented in this embodiment by the line S). With the leading end 51 in a desired position, one or more regions of the needle 30 are deformed or otherwise caused to change shape to impinge upon and secure the internalized portion of the segment 50. As illustrated in FIG. 2, some deformed regions 60 can be located between the distal end 35 and the first hole 71, while others are located between the first hole 71 and the second hole 72.

With reference now to FIG. 3(a), shown is a cross sectional view of tissue augmentation device 20 taken along the view line 2-2 shown in FIG. 2. The cannulated, elongate portion 31 has an inner surface 40 and an outer surface 41. As shown in the current illustration, the deformations 60 can be formed by applying approximately equal forces F to the outer surface 41 of the elongate portion 31 in the direction of the arrows. The forces F bend portions of the outer surface 41 and inner surface 40 radially inward (i.e., toward the center 39 of the elongate portion 31), which in turn, compress portions of the segment of material 50 received within the needle 30.

In certain embodiments, the deformations 60 are formed with a crimping device. Nonetheless, it should be understood that the deformations 60 can be formed in any suitable manner. In fact, a variety of techniques, alone or in combination, can be used, including but not limited to indenting, impressing, squeezing, and bending. Further, the present invention contemplates tissue augmentation devices that have any suitable number of deformations 60 being positioned at any suitable location on the elongate portion 31. In some desirable embodiments of the invention, the deformed or other implant-retaining shaped region(s) of the cannula walls is/are of such a nature that no substantial increase in tissue penetrating resistance is incurred due to the region(s). This can include, in certain inventive forms, such region(s) having a maximum cross-sectional dimension substantially the same as or less than that of adjacent regions of the needle 30. It will be understood however that such features are not necessary in all embodiments of the present invention.

Thus, the size, shape, and configuration of the deformations 60, as well as their location and orientation on the needle 30, can vary in accordance with several factors including, as examples, the requirements of a particular application, technique, procedure, or patient. As described below in relation to illustrative FIGS. 6(a)-(c), the deformations 60 can occur inwardly and are configured to constrict and prevent the segment of material 50 and needle 30 from disengaging as the needle passes through a patient's tissue. Accordingly, it may be desirable to deform the needle 30 to varying degrees depending on the characteristics desired of the final device 20 and/or the environments that it will face during use. For example, FIG. 3(b) shows a tissue augmentation device 20 embodiment that is substantially similar to that of FIG. 3(a), except in respect of the deformations 60. In this embodiment, the deformations 60 are larger, i.e., portions of the outer surface 41 and inner surface 40 are forced closer to the center 39 of the elongate portion 31.

As well, the deformations 60 can be formed any time before the tissue augmentation device 20 is used in an augmentation procedure. Preferably, a surgeon receives a device 20 with the deformations 60 already formed to constrict the segment of material 50, although the present invention also contemplates that a surgeon or other healthcare provider could assemble the needle 30 and segment 50 together and form the deformations 60 prior to the augmentation procedure. Also, although the deformations 60 depicted in FIGS. 3(a)-(b) have a generally rounded, trough-like shape from a cross-sectional point of view, it should be understood that the deformations 60 can have any suitable shape to suitably constrict portions of the segment of material 50 received within the needle 30, e.g., triangular, rectangular, and the like. Yet, it also should be understood that certain aspects of the present invention involve ways to join together an implant material and a tissue penetrating member without having to necessarily deform the tissue penetrating member, as is discussed elsewhere herein.

Figure 4:
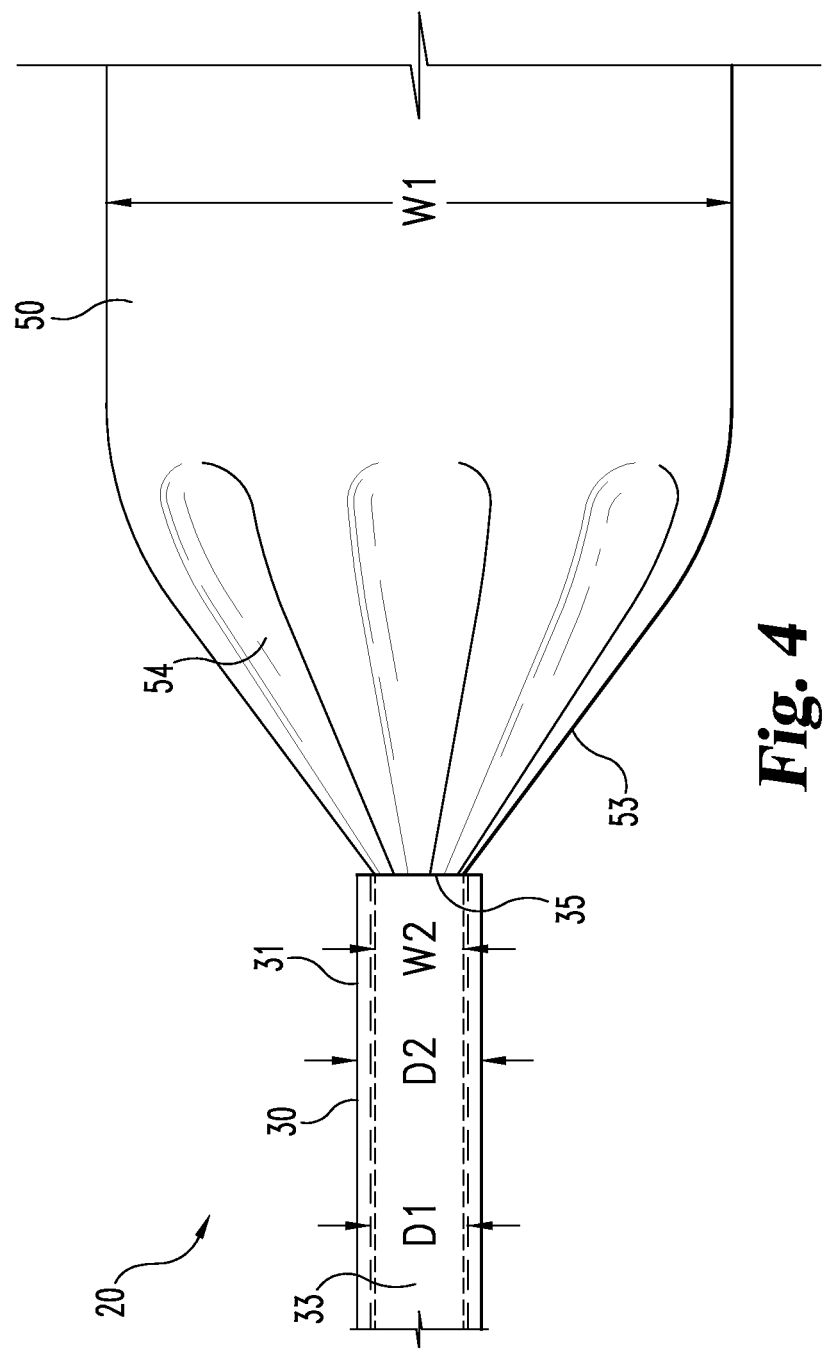
FIG. 4 is a partial, front view of the tissue augmentation device of FIG. 1.

FIG. 4 is a partial, top view of the tissue augmentation device 20 of FIG. 1, highlighting an area of the device 20, wherein a portion of the segment of material 50 is received within the distal end 35 of the elongate body portion 31. The generally cylindrical, elongate body portion 31 can have any suitable inside and outside diameter. In certain embodiments, the needle 30 will be a 20 to 10 gauge needle, e.g. having a cannulated body with an inside diameter D1 of about 0.5 mm to about 2.5 mm, more typically in the range of about 1 mm to about 1.5 mm, and an outside diameter D2 of about 0.75 mm to about 2.75 mm, more typically in the range of about 1.25 mm to about 1.75 mm. In certain specific embodiments, the elongate portion 31 provides a 16 gauge cannulated needle body having a wall thickness of about 0.25 mm (about 0.01 inch). The needle 30 can have any suitable length, for instance ranging from about 5 cm to about 30 cm, more typically in the range of about 8 cm to about 20 cm. Also, the needle 30 need not be straight in all embodiments, but may be curvilinear or otherwise shaped to better suit the requirements of a particular technique or patient.

The portion of the segment of material 50 received within the needle 30 has a first width W1 before it is drawn into the needle 30, and a second width W2 (approximately equal to the inside diameter D1 of the elongate portion 31) after it is drawn into the needle 30. The width W2 is less than the width W1, because as the segment's leading end 51 is drawn into the needle 30, portions of the segment 50 gather by rolling and/or folding over each other one or more times, and thereby generally conform to the inside diameter D1 of the elongate portion 31. A tapered transition region 53 forms in the segment of material 50 proximate the distal end 35 but outside of the needle 30. The transition region 53 includes gathered material, e.g. a plurality of folds 54, and has an external profile of decreasing width or dimension in a direction toward the trailing end 35 of the needle 30.

The internalized portion of the segment of material 50 can be moved into position within the needle 30 in any suitable manner. In one example, a funneling device can used to help gather and guide the segment 50 into the needle 30. In this case, one end of a pulling instrument such as a wire can be passed through the slot 70 and guided out of the distal end 35 of the elongate portion 31. This same end of the instrument is then guided through the narrow end of a funnel and connected to the segment of material 50 proximate the segment's leading end 51. Thereafter, the segment of material 50 is drawn into the distal end 35 of the elongate portion 31 by pulling the instrument back through the slot 70. The narrowing funnel walls can thereby cause the segment of material 50 to roll or fold over itself one or more times, desirably in a generally regular pattern, as the segment 50 enters the needle 30. The walls of the needle 30 can thereafter be crimped or otherwise be caused to change in shape or position to secure the needle 30 to the segment 50. In embodiments including a flexible covering, it will be understood that the techniques for internalizing a segment of material will similarly apply to the flexible covering.

Figure 9:
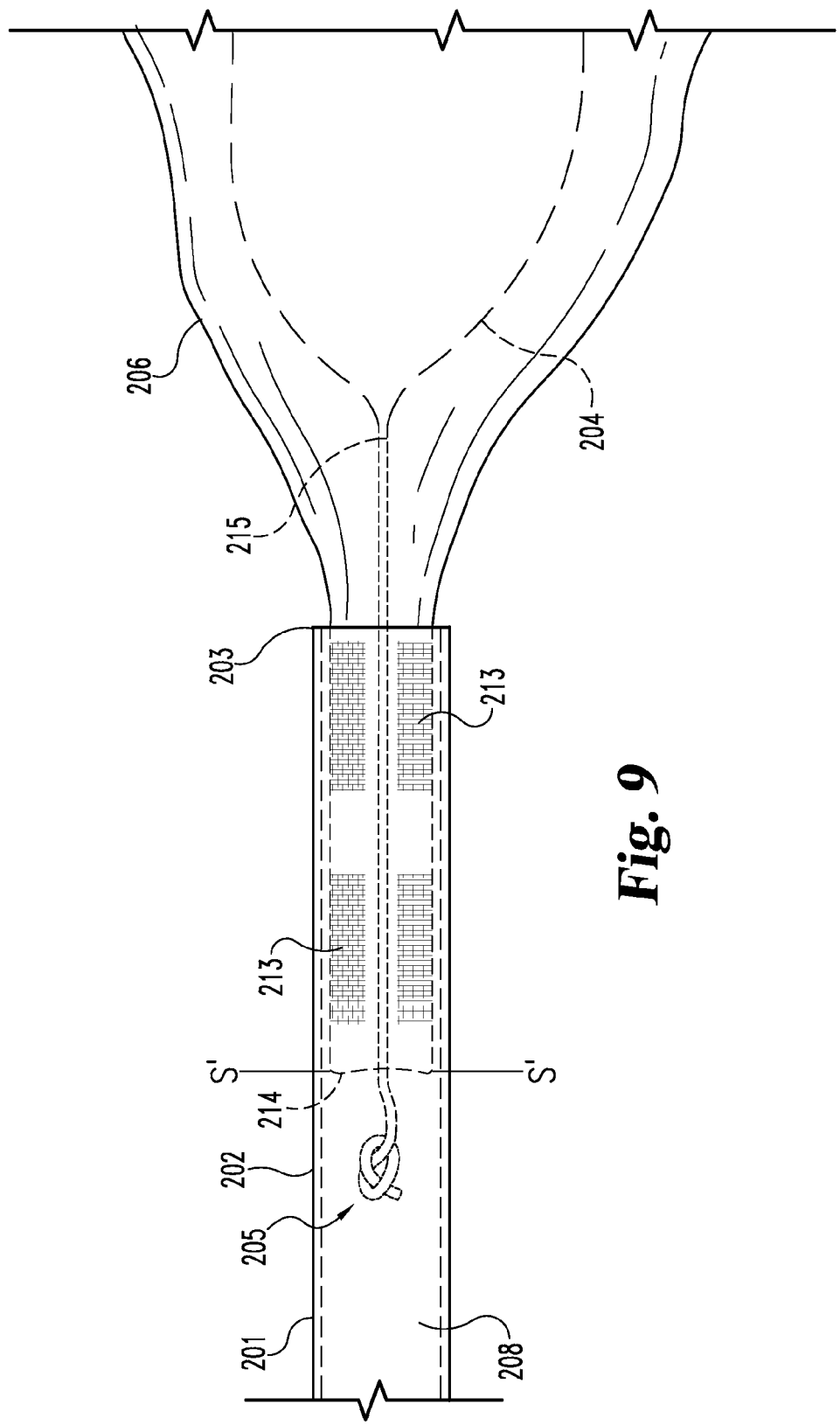
FIG. 9 is a partial, enlarged top view of the tissue augmentation device of FIG. 8.

With reference now to FIG. 9, shown is a partial, top view of the tissue augmentation device 200 depicted in FIG. 8, highlighting an area of the needle 201 proximate the distal end 203 of the elongate portion 202. The needle 201 provides a plurality of deformed regions 213 proximate the distal end 203 of the elongate portion 202. The deformations 213 are configured to constrict portions of the flexible covering 206 received within the needle 201. The deformations 213 also function to prevent suture 205 from exiting the distal open needle end 203. During one illustrative tissue augmentation device 200 manufacturing process, the leading end 214 of flexible covering 206 can be drawn into the needle 201 in a gathered configuration (e.g., rolled, folded, and/or twisted) until it reaches a desired point within the elongate portion 202 (represented in this embodiment by the line S'). With the leading end 214 in a desired position, one or more regions of the needle 201 are deformed or otherwise caused to change shape to impinge upon and secure the internalized portion of the flexible covering 206. The inner wall 208 of the elongate portion 202 provides a plurality of deformed regions 213 that are configured to compress and secure portions of the covering received within the needle. In certain embodiments, suture 205 is not included, and segment of material 204 is positioned within the flexible covering 206 such that both the flexible covering 206 and the segment of material 204 are secured by the deformations 213. As before, the deformations 213 can be formed with a crimping device or any other suitable manner, and any suitable number of deformations 213 can be positioned at any suitable location on the elongate portion 202. In the embodiment depicted, a suture 205 can be included to indirectly attach the segment of material 204 to the needle 201 as described previously. Suture 205 extends from the leading end 215 of the segment of material 204 through distal open end 203 and past deformations 213. The end of the suture can be tied in a knot or is otherwise adapted such that it is sufficiently large enough to prevent its passage back through distal open end 203.

The flexible covering can be directly secured to the needle by either being suitably received within needle or fixed along the outside surface of needle. In embodiments where the covering is designed to fit along the outer wall of the needle, a portion of the flexible covering can be retained at its position on the outside of the needle by any suitable means. For example, the covering can be glued or heat shrunk to fix a portion of the covering onto the needle. In some forms, a flexible covering is received over a segment of a tissue penetrating device having cannulated portions and/or non-cannulated portions. Additionally or alternatively, the portion of the flexible covering adapted to be fixed to the needle can be made of an elastic material such that the material generally conforms to the outer surface of the needle. In either case, once the tissue augmentation device is delivered to its desired location, all or a portion of the covering can be separated from the remainder of the tissue augmentation device; thus leaving the segment of material in place to augment a desired tissue.

Figure 10:
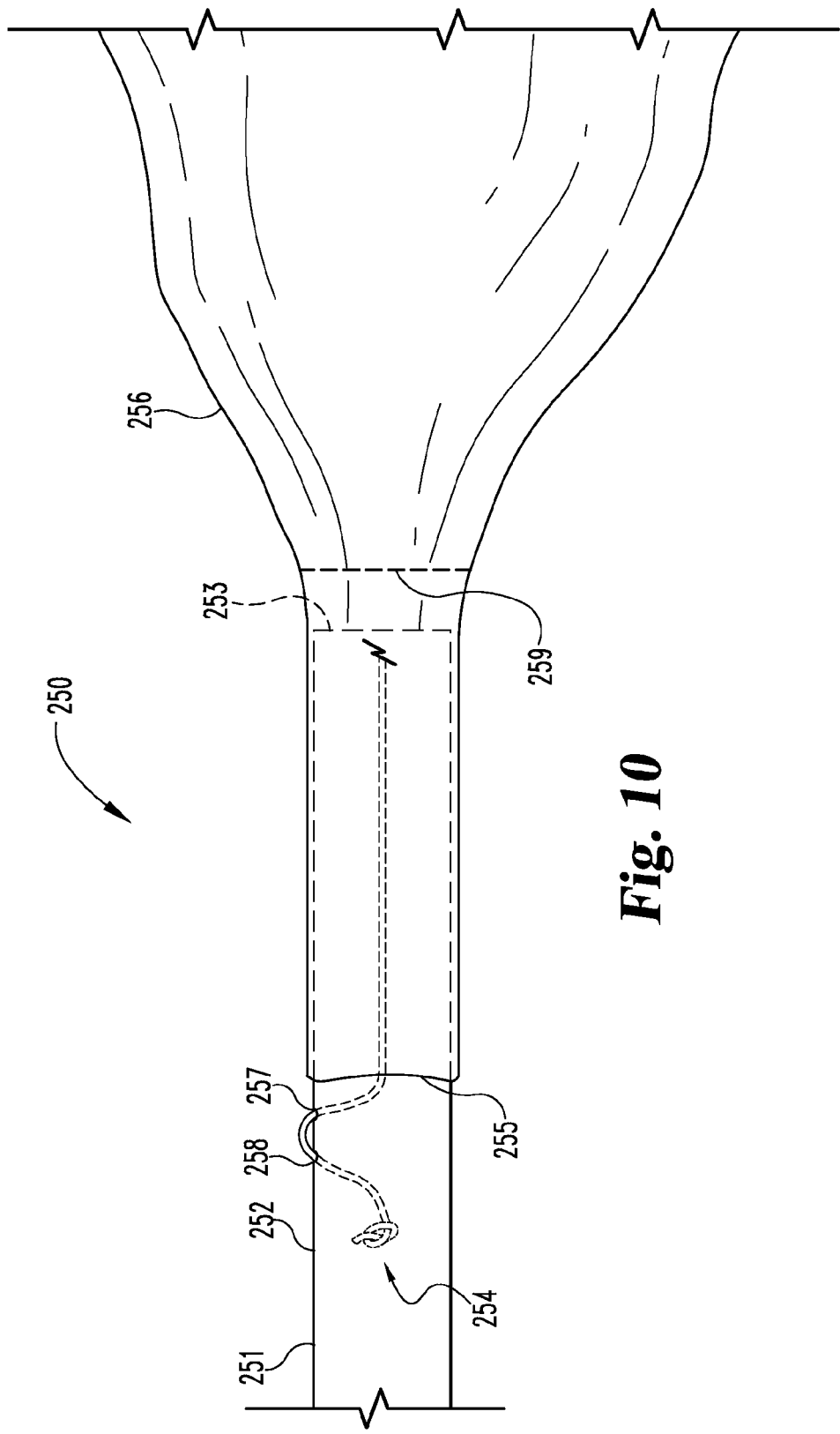
FIG. 10 is a partial, enlarged top view of another alternative tissue augmentation device of the invention.

With reference now to FIG. 10, shown is a partial, top view of an alternate tissue augmentation device of the invention, highlighting an area of the needle 251 proximate the distal end 253 of the elongate portion 252. In this region, the needle 251 has a first opening 257 and a second opening 258, each of which are defined in the wall of the elongate portion 252. Such holes may be machined or otherwise processed into the needle using known techniques, including for instance electrical discharge machining (EDM), and may occur at any suitable location on the needle and relative to each other in addition to what is shown. Further, first hole 257 and second hole 258 are located and aligned on one side of the needle 251, along a substantially straight line C (not shown) from the proximal end (hidden in FIG. 10) to the distal end 253 of the elongate portion 252. Suture 254 extends from the leading end of the segment of material (hidden in FIG. 10) through the distal end 253 of elongate portion 252 until it reaches first hole 257. Suture 254 extends out of elongate portion 252 through first hole 257 and back into the cannulated body of elongate portion 252 through second hole 258. To secure the segment of material to the elongate portion 252 of needle 251, the end of suture 254 is tied in a knot or is otherwise adapted such that is sufficiently large enough to prevent its passage back through second hole 258. Leading end 255 of flexible covering 256 is received over a portion of needle 251 including elongate portion distal end 253, and held in place along the needle by its elastic properties.

In some embodiments, the present invention provides a flexible covering having an adaptation to facilitate separation of a flexible covering portion from the remainder of the tissue augmentation device during an implantation step. Illustratively, a flexible covering can have a weakened portion such as the perforation 259 depicted in FIG. 10 to facilitate a tear-away operation to remove a portion of the covering from the device. Such a weakened portion may include any suitable means for facilitating tearing or breaking along the area, including for example scores, thinner portions, and the like. These and other adaptations for facilitating separation of the covering material will be recognized by the skilled artisan and are encompassed by the present invention. These perforations or other weakened portions can serve to provide a location for more predictably separating one portion of the flexible covering from another.

Figure 5:
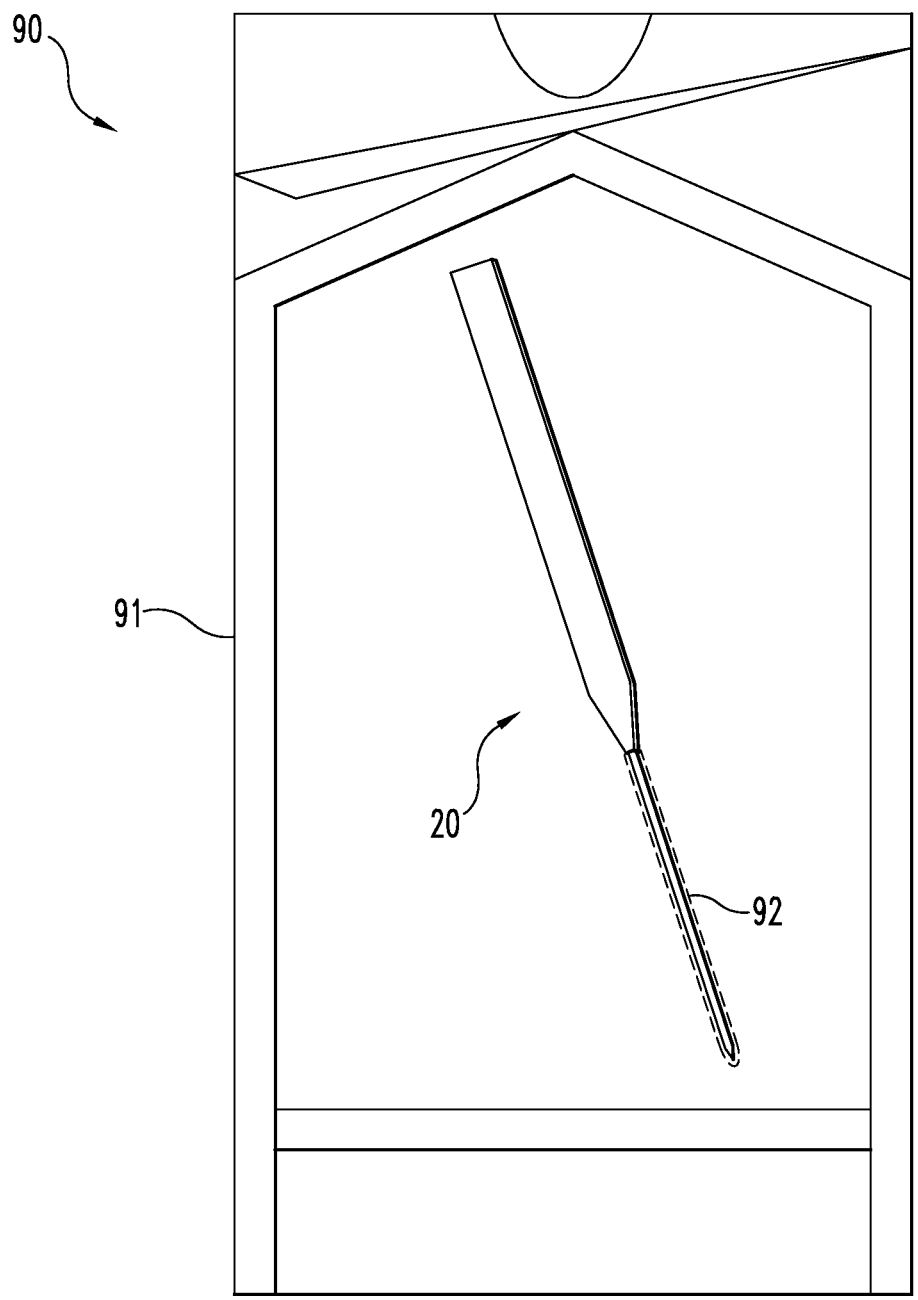
FIG. 5 is a top view of a tissue augmentation kit.

With reference now to FIG. 5, illustrated a medical product 90 of the invention that includes a sealed double pouch package 91 and a tissue augmentation device 20 as in FIG. 1 received therein. It will be understood that other packaging modes can also be undertaken, including for example the use of other flexible packaging configurations, more rigid trays to hold and protect the device 20, and the like. As well, if needed, a protective sleeve or cover 92 (shown by dotted lines) can be positioned over all or a portion of the needle 30 and particularly over the tip portion thereof. The packaged tissue augmentation product 90 can be terminally sterilized. Such sterilization can be achieved via irradiation, ethylene oxide gas, or another suitable sterilization technique. Also, the device 20 and particularly material segment 50 can be in any suitable state (e.g., hydrated, dehydrated, or partially dehydrated). The device 20 and particularly material segment 50 can be dehydrated or partially dehydrated by any means known in the art (e.g., lyophilization or air dried). The package 90 can be marked to communicate the contents of the package to a person, machine, computer, and/or electronic device. Such markings may include the size or dimensions of the device 20, the type of materials used to form the device 20, and/or the device's physical state. The package may also contain written material providing instructions for use of the device in a tissue (e.g. lip) augmentation procedure.

FIGS. 6(a)-(c) illustrate steps of a method of augmenting tissue of a patient with the tissue augmentation device 20 of FIG. 1. It will be understood that this method can generally be followed for any tissue augmentation device described herein, including tissue augmentation device 200 of FIG. 8. One step of the method includes inserting the first end 36 of the needle's tapered portion 32 into a volume of patient tissue 110 through an entry point 111 in the patient's skin (see FIG.

Figure 7:
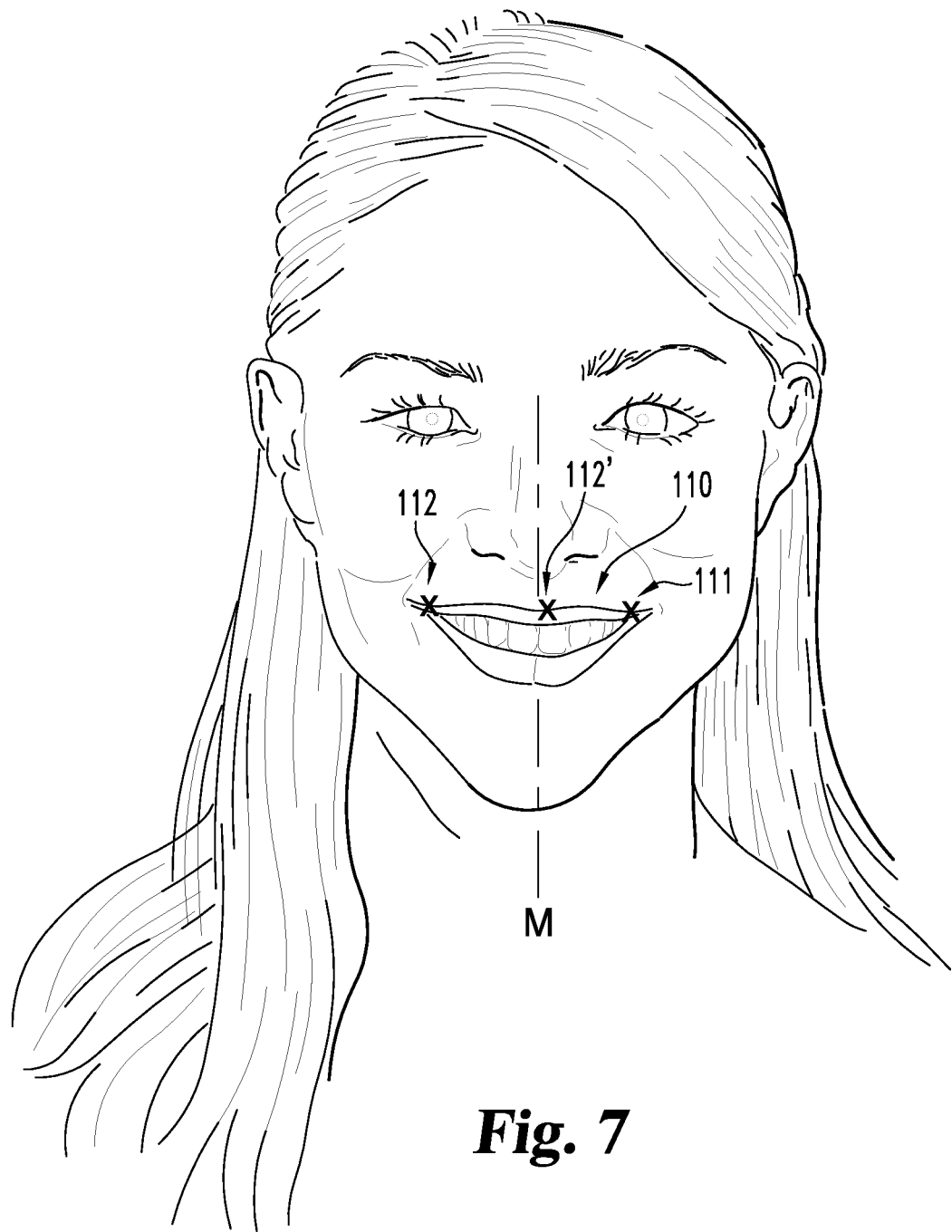
FIG. 7 illustrates a human lip region that can be augmented in methods of the invention.

6(*a*)). The volume of patient tissue 110 may comprise any suitable tissue. For example, and as shown in FIG. 7, the volume of patient tissue 110 may comprise a human upper lip. In other embodiments, the volume of patient tissue may comprise a lower lip, forehead, cheek, eyelid, ear, throat, neck, chin, nose, nasal labial fold, scalp, hand, arm, foot, ankle, leg, buttocks, abdomen, shoulder, back, breast or any other part of a patient.

Continuing with the illustrative method, after the first end 36 of the needle's tapered portion 32 is inserted into the volume of patient tissue 110 through the entry point 111, the needle 30 is carefully guided through the volume of tissue 110 toward an exit point 112 in the patient's skin. In this illustrative embodiment, the length of the needle 30 is such that the first end 36 of the needle's tapered portion 32 exits the volume of tissue 110 through the exit point 112 before the trailing end of the needle 30 is drawn into the volume of tissue 110 (See FIG. 6(*b*)). In embodiments wherein the needle 30 includes a cutting needle tip, the passageway 113 can be formed as the needle 30 advances through the volume of tissue 110 and cuts through native tissue. In other embodiments a pre-formed tract could be provided, and the tissue penetrating member equipped with a non-cutting (e.g. bullet) tip to traverse the pre-formed tract. In some cases, the segment 50 is configured in such a manner that it is forced to roll up and/or fold to conform to the inside of the passageway 113.

After the needle 30 is withdrawn from the volume of tissue 110 through the exit point 112, a portion of the segment of material 50 remains in the volume of tissue 110 along the passageway 113. As shown in FIG. 6(*c*), other portions of the segment 50, e.g. the leading end 51 and trailing end 52, are located outside the volume of tissue 110. Such aspects are not needed in all embodiments of the invention, though, e.g. the trailing end 52 could be drawn into the volume of tissue 110 during the tissue augmentation procedure.

Continuing with reference to FIG. 6(*c*), an implant-forming element 114 is provided by separating a portion of the segment of material 50, including the segment's leading end 51 (see FIG. 2), from the tissue augmentation device 20 after the needle 30 is withdrawn from the volume of tissue 110. In other embodiments, the implant-forming element 114 can include the entire segment of material 50 (i.e. the entire segment of material 50 is separated from the needle 30 after the needle 30 is withdrawn from the volume of tissue 110). In still further embodiments, all or a portion of the segment of material 50 (e.g. an unneeded portion of its trailing end) could be separated from the tissue augmentation device 20 before the needle 30 is completely withdrawn from the volume of tissue 110. As well, any portion of the implant-forming element 114 separated from the tissue augmentation device 20 may be further manipulated after it is separated from the device 20. For example, both end regions of the implant-forming element 114 may be cut or trimmed and positioned with their remaining ends just below the surface of the skin so that the implant-forming element 114 is located entirely inside the volume of tissue 110. In embodiments where a flexible covering is used, said covering will be removed as well. If a suture or other attachment means is present, the segment of material will be detached from the attachment means, preferably at the site of implantation. These and other potential variations in the implant procedure will be apparent to those of ordinary skill in the art from the descriptions herein.

In these and other inventive procedures, flexible coverings such as those depicted in FIGS. 8 and 10 may be useful to provide (or at least help provide) a barrier between the tissue augmentation material and contaminants which may be present at the implantation site such as bacteria or cells located on outer surfaces of the patient's skin or on other non-sterile surfaces or objects. In some embodiments, a flexible cover that is received over a segment of implant material remains over the material segment as the implant material is desirably positioned within a volume of patient tissue. Then, while holding the implant material generally stationary, the flexible covering can be withdrawn from the implantation site, for example, by being pulled back through the passageway formed in the volume of tissue, to leave the tissue augmentation material implanted. In other embodiments, an open, leading end of a flexible covering can be positioned at or just inside an entry point in a volume of patient tissue. Then, all or a portion of the flexible covering can be separated from the remainder of the tissue augmentation device (e.g., by tearing the covering material along a perforated portion), while still holding this portion in position to maintain the barrier between the implant material and possible contaminants at the implantation site. Thereafter, the implant material can be pulled through the flexible covering and into the volume of patient tissue, and the flexible covering can be discarded.

Figure 13:
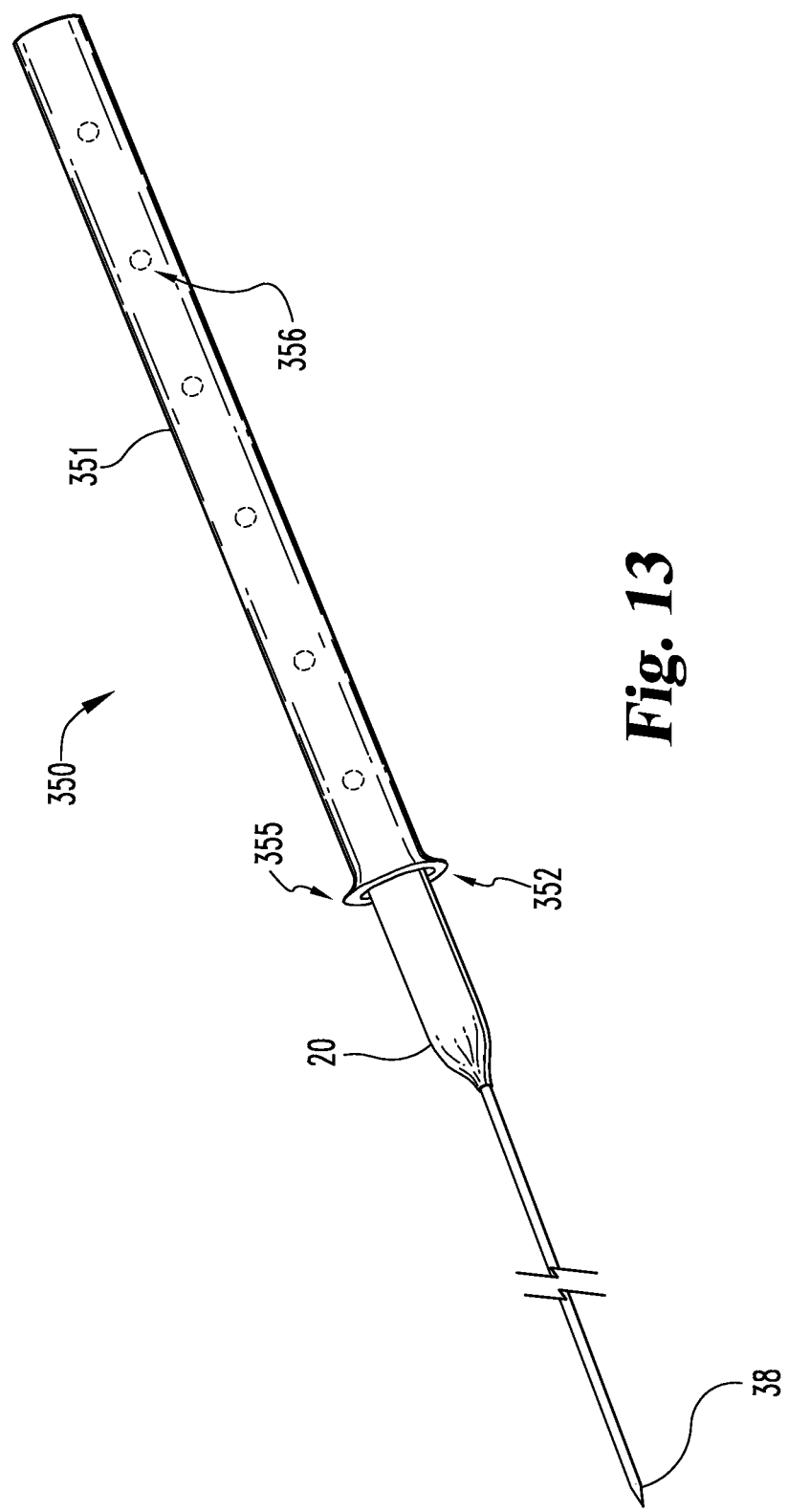
FIG. 13 is a perspective view of still another tissue augmentation device of the invention.

Inventive medical products, in certain embodiments, will incorporate a rigid, semi-rigid or otherwise non-highly flexible protective sheath or other protective member into which a tissue augmentation device can be at least partially received. Referring now to FIG. 13, shown is an inventive medical product 350 that includes the tissue augmentation device 20 of FIG. 1 in combination with a protective sheath 351. Sheath 351 is generally cylindrical, and includes an open end 352 that communicates with a hollow interior of the sheath. FIG. 13 shows tissue augmentation material partially extending from the hollow sheath interior through open end 352. Protective members of this sort can be adapted to accommodate all or part of a tissue augmentation device, and may be useful to provide (or at least help provide) a barrier between the tissue augmentation device and contaminants which may be present at the implantation site as described elsewhere herein. In some inventive methods, an open, leading end of a protective sheath such as that shown can be positioned at an entry point in a volume of patient tissue, and then held there while implantable material is drawn from the sheath and into the volume of patient tissue. A flared portion 355 is optionally included at open end 352, and may help prevent the protective sheath from entering the volume of patient tissue along with the tissue augmentation material. Openings 356 (shown in phantom) are also optional, and can allow for access to the contained device, such as to allow for rehydration or further sterilizing of the device.

Tissue augmentation devices of the invention, especially those incorporating porous or otherwise absorbent implant material segments 50 and 204, such as ECM or collagenous materials, can advantageously be used with the segment 50 or 204 in a hydrated condition. Hydration can be achieved with any suitable liquid, typically an aqueous medium such as sterile water, saline, or the like. The wetting medium may also include other therapeutic substances, such as antibiotics, anesthetics and/or other pharmaceuticals. Contact between the wetting agent and the segment 50 or 204 can be achieved in any suitable fashion, including immersion such as dipping or soaking, spraying, etc. Further, the wetting agent along with any active ingredients such as antibiotics can be delivered to a portion of segment 50 or 204 internalized in the needle by wicking and/or through hole(s) (e.g. holes 71 and 72 or 257 and 258, respectively) and/or slots (e.g. 70) in the walls of the needle.

The tissue augmentation devices of the invention can be provided for a variety of augmentation or restoration procedures. As illustrated in FIG. 7, the volume of patient tissue 110 may occur in the region of a human upper lip. In this case, the entry point 111 and exit point 112 are located approximately equal distances from the lip's midline M in the mucosal part of the upper lip. Nonetheless, it is understood that the entry point 111 and exit point 112 can be placed in any desired location on or near the lip. Also, there can be more than one entry point 111 and more than one exit point 112. For instance, a method may involve augmenting upon only one side of an upper lip. In this case, a second, alternate exit point 112' is located on the mucosal part of the lip near the lip's midline M (as shown in FIG. 7). Augmenting less than a full lip may be desirable or necessary because of the shape of the lip and/or the nature of the underlying lip tissue. In general, the location of any entry point or exit point may depend on factors, such as but not limited to, the size and shape of the native lip, the extent of augmentation being performed, the desired cosmetic outcome, and the like.

It should also be noted that the relative softness and/or thickness of different regions of the implant-forming element 114 can be varied to suit the requirements of a particular procedure, technique, or patient. Still further, in certain embodiments, a method of augmenting lip tissue includes prepping the perioral area in a sterile manner and administering a local anesthetic, such as lidocaine with epinephrine, to a lip and/or areas around a lip. Once the implant-forming portion is implanted in a suitable location, an antibiotic ointment is applied to the punctures at the entry and exit points to reduce the risk of infection. Thereafter, a bandage, or possibly even sutures, are applied to the entry and exit points. Further, ice can be applied indirectly to the implantation site to further aid in the healing process. It will be understood that similar steps of preparing and anesthetizing surgical sites and/or similar post-surgical techniques can be undertaken in other tissue augmentation procedures in accordance with the present invention.

All publications and patent applications cited in this specification are herein incorporated by reference as if each individual publication or patent application were specifically and individually indicated to be incorporated by reference. Further, any theory, mechanism of operation, proof, or finding stated herein is meant to further enhance understanding of the present invention, and is not intended to limit the present invention in any way to such theory, mechanism of operation, proof, or finding. While the invention has been illustrated and described in detail in the drawings and foregoing description, the same is to be considered as illustrative and not restrictive in character, it being understood that only selected embodiments have been shown and described and that all equivalents, changes, and modifications that come within the spirit of the inventions as defined herein or by the following claims are desired to be protected.

What is claimed is:

1. A device for introducing implant material into soft tissue of a patient, the device comprising:
    an implantable material including a rolled sheet material, said implantable material having a length between a leading end of said implantable material and a trailing end of said implantable material, wherein the rolled sheet material comprises an extracellular matrix sheet material harvested from a collagenous tissue source;
    a tissue-penetrating member, said tissue-penetrating member having a length between a leading end of said tissue penetrating member and a trailing end of said tissue penetrating member; and wherein said tissue-penetrating member is attached to said implantable material by an intermediate material, said intermediate material attached to and extending between said trailing end of said tissue penetrating member and said leading end of said implantable material.

2. The device of claim 1, wherein the extracellular matrix material comprises submucosa, serosa, pericardium, dura mater, peritoneum, or dermal collagen.

3. The device of claim 1, wherein the rolled sheet material provides spiral layers.

4. The device of claim 3, wherein the spiral layers are compressed and bonded so as to form a substantially unitary structure.

5. The device of claim 1, wherein at least a portion of said implantable material is configured for augmentation of human facial tissue.

6. The device of claim 1, wherein a rolled or non-rolled sheet portion of the implantable material is secured to the tissue-penetrating member.

7. The device of claim 6, wherein said implantable material exhibits a non-cylindrical shape.

8. The device of claim 6, wherein said implantable material includes a leading tapered region.

9. The device of claim 1, wherein at least a portion of the implantable material extends beyond the trailing end of the tissue-penetrating member for following said trailing end through a volume of patient tissue traversed by said tissue-penetrating member.

10. The device of claim 1, wherein said rolled sheet material comprises one or more layers of overlapping material which have been bonded to form a volumetric body.

11. The device of claim 10, wherein said layers of overlapping material have been compressed and dried to bond the layers together.

12. The device of claim 1, wherein said length of said implantable material is greater than said length of said penetrating member.

13. A device for introducing implant material into soft tissue of a patient, the device comprising:
    a leading portion having a leading end including a tissue-penetrating member, and a trailing end, wherein said leading portion is configured to traverse a volume of patient tissue such that a passageway through the volume of patient tissue is formed after said trailing end of said leading portion has passed therethrough; and
    a trailing portion extending distally from said trailing end of said leading portion, said trailing portion including a rolled sheet material, wherein the rolled sheet material comprises an extracellular matrix sheet material harvested from a collagenous tissue source,
    wherein said leading portion is effective to draw at least a portion of said trailing portion into the volume of patient tissue along the passageway traversed by said tissue-penetrating member.

14. The device of claim 13, further comprising an intermediate portion connecting said leading portion to said trailing portion.

15. The device of claim 14, wherein said intermediate portion comprises a suture.

16. The device of claim 14, wherein said intermediate portion includes an extension of the rolled sheet material affixed to the tissue-penetrating member.

17. The device of claim 16, wherein said rolled sheet material includes a tapered longitudinal portion.

18. The device of claim 16, wherein said rolled sheet material provides a three-dimensional body exhibiting a non-cylindrical shape.

19. The device of claim 13, wherein a portion of the rolled sheet material is secured to the tissue-penetrating member.

20. A device for introducing implant material into soft tissue of a patient, the device comprising:
- a tissue-penetrating member having a leading end and a trailing end;
- an implantable body secured to the tissue-penetrating member and including a rolled sheet material, wherein the rolled sheet material comprises an extracellular matrix sheet material harvested from a collagenous tissue source; and
- wherein said tissue penetrating member is configured for advancement through patient tissue with at least a portion of the implantable body trailing behind the trailing end of the tissue-penetrating member such that said rolled sheet material trails behind the trailing end of the tissue-penetrating member.

* * * * *